(12) United States Patent
Asada et al.

(10) Patent No.: US 8,348,828 B2
(45) Date of Patent: Jan. 8, 2013

(54) MEDICAL APPARATUS AND OPERATION METHOD FOR INTRODUCING MEDICAL APPARATUS INTO BODY

(75) Inventors: Daisuke Asada, Hachioji (JP); Sho Nakajima, Hachioji (JP); Hideaki Kinouchi, Hachioji (JP); Nobuyoshi Yazawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 350 days.

(21) Appl. No.: 12/839,678

(22) Filed: Jul. 20, 2010

(65) Prior Publication Data

US 2011/0046440 A1 Feb. 24, 2011

Related U.S. Application Data

(63) Continuation of application No. PCT/JP2010/057268, filed on Apr. 23, 2010.

(30) Foreign Application Priority Data

Aug. 24, 2009 (JP) ................................ 2009-193479

(51) Int. Cl.
*A61B 1/00* (2006.01)
(52) U.S. Cl. ........................ 600/104; 606/108; 600/110
(58) Field of Classification Search .................. 600/103, 600/106, 112, 114, 118, 172–175
See application file for complete search history.

(56) References Cited

U.S. PATENT DOCUMENTS

| | | | |
|---|---|---|---|
| 2005/0085697 A1 | 4/2005 | Yokoi et al. | |
| 2005/0165272 A1* | 7/2005 | Okada et al. | 600/114 |
| 2008/0015413 A1* | 1/2008 | Barlow et al. | 600/114 |
| 2008/0177141 A1* | 7/2008 | Wu et al. | 600/112 |
| 2008/0309758 A1* | 12/2008 | Karasawa et al. | 348/65 |
| 2008/0312502 A1 | 12/2008 | Swain et al. | |
| 2009/0187073 A1* | 7/2009 | Karasawa et al. | 600/114 |
| 2010/0016664 A1* | 1/2010 | Viola | 600/114 |
| 2010/0217080 A1* | 8/2010 | Cheung et al. | 600/121 |

FOREIGN PATENT DOCUMENTS

| | | |
|---|---|---|
| EP | 1 671 575 A1 | 6/2006 |
| EP | 1 992 271 A1 | 11/2008 |
| JP | 07-250809 | 10/1995 |
| JP | 2003-210393 | 7/2003 |
| JP | 2005-103092 | 4/2005 |
| JP | 2007-020809 | 2/2007 |
| JP | 2008-307224 | 12/2008 |
| JP | 2009-517167 | 4/2009 |
| WO | WO 2007/063550 A2 | 6/2007 |
| WO | WO 2007/097393 A1 | 8/2007 |

OTHER PUBLICATIONS

International Search Report dated May 25, 2010.

* cited by examiner

*Primary Examiner* — Thomas J Sweet
*Assistant Examiner* — Kevin G Barry, III
(74) *Attorney, Agent, or Firm* — Scully Scott Murphy & Presser, PC

(57) ABSTRACT

A medical apparatus which is introduced into a body includes an image pickup unit that picks up an image of the interior of the body, a communication cable that sends/receives a signal to/from an external device, an electric terminal section disposed at an end section of the communication cable, a drip-proof cap attached so as to cover the electric terminal section, a locking section provided at the drip-proof cap that locks a puncture needle for pulling the communication cable introduced into the body out of the body, and a dissection section provided at the drip-proof cap that dissects a body wall tissue when the cable wire is pulled out.

7 Claims, 24 Drawing Sheets

MEDICAL APPARATUS AND OPERATION METHOD FOR INTRODUCING MEDICAL APPARATUS INTO BODY

CROSS REFERENCE TO RELATED APPLICATION

This application is a continuation application of PCT/JP2010/057268 filed on Apr. 23, 2010 and claims benefit of Japanese Application No. 2009-193479 filed in Japan on Aug. 24, 2009, the entire contents of which are incorporated herein by this reference.

BACKGROUND OF THE INVENTION

1. Field of the Invention

The present invention relates to a medical apparatus provided with an image pickup apparatus to be introduced into the body and an operation method for introducing the medical apparatus into the body.

2. Description of the Related Art

As is generally known, endoscope apparatuses, which are medical apparatuses, are provided with an image pickup apparatus, designed to be introduced into a body cavity of a patient and carry out various kinds of inspections and treatment or the like of affected areas in the body based on observed images photographed by the image pickup apparatus.

Examples of such endoscopes include those introduced into digestive organs such as esophagus, stomach, large intestine, duodenum, which are tube cavities and tubes in the body from the oral cavity or anus and those introduced into the abdominal cavity from the vicinity of the umbilical region by puncturing through the body wall and, in addition, surgical operations that conduct therapy or treatment while observing organs in the body, so-called laparoscopic surgery are becoming a focus of attention.

This laparoscopic surgery is a low-invasive operation without requiring any large-scale abdominal operation, and can thereby perform treatment by puncturing, through the abdomen of the patient, a trocar that guides an observation endoscope into the body cavity and a trocar that guides a treatment instrument to a treatment region and introducing the endoscope into the abdominal cavity of the patient.

As the above-described medical apparatus introduced into the body, a capsule apparatus is disclosed as described, for example, in Japanese Patent Application Laid-Open Publication No. 2007-20809, in which an ultrasound capsule is detachably connected to a free end of a signal cable via a connector so that the ultrasound capsule is detachable from the signal cable.

Even when bent portions and narrowed portions of tubes of in-body tubes prevent the ultrasound capsule from passing, this conventional capsule apparatus is designed to prevent such obstruction from causing pain to the patient or prevent a signal cable from suffering wire breakage and allow the ultrasound capsule to be discharged out of the body.

Furthermore, for example, Japanese Patent Application Laid-Open Publication No. 7-250809 discloses an apparatus provided with a solid hollow shaft having an at least partially transparent penetrating distal end portion at a far end for penetration of a body tissue which can be provided with illumination and visualization members.

This conventional apparatus for penetrating a body tissue allows the tissue to be observed through the transparent member at the distal end portion before penetrating or removing the tissue or the like using a trocar or the like.

SUMMARY OF THE INVENTION

A medical apparatus according to an aspect of the present invention is a medical apparatus introduced into a body, including an image pickup unit that picks up an image of the interior of the body, a communication cable that sends/receives a signal to/from an external device, an electric terminal section disposed at an end of the communication cable and electrically connected to the external device, a drip-proof cap attached so as to cover the electric terminal section and be detachably attached to the electric terminal section, a locking section provided at the drip-proof cap that locks a puncture needle for pulling the communication cable introduced into the body out of the body, and a dissection section provided at the drip-proof cap that dissects a body wall tissue when the communication cable is pulled out of the body by the puncture needle.

A medical apparatus according to another aspect of the present invention is a medical apparatus introduced into a body, including image pickup means for picking up an image of the interior of the body, communication means for sending/receiving a signal to/from an external device, electric connection means disposed at an end of the communication means and electrically connected to the external device, drip-proof means attached so as to cover the electric connection means and be detachably attached to the electric connection means, locking means provided at the drip-proof means for locking puncture means for pulling the communication means introduced into the body out of the body, and dissection means provided at the drip-proof means for dissecting a body wall tissue when the communication means is pulled out of the body by the puncture means.

Furthermore, an operation method for introducing the medical apparatus into a body according to an aspect of the present invention attaches a drip-proof cap to an electric terminal section provided at an end of a communication cable that sends/receives a signal to/from an external device provided in the medical apparatus, introduces the medical instrument into the body, punctures a puncture needle so as to penetrate the body wall into the body into which the medical instrument has been introduced, locks a hook of the puncture needle at the locking section while photographing an image of the locking section provided at the drip-proof cap using the image pickup unit, pulls the puncture needle out of the body, pulls the communication cable out of the body while dissecting the body wall through a dissection section provided at the drip-proof cap, takes the drip-proof cap out of the electric terminal section and electrically connects the electronic terminal section to the external device.

DETAILED DESCRIPTION OF THE PREFERRED EMBODIMENTS

Hereinafter, embodiments of the present invention will be described with reference to the accompanying drawings. In the following descriptions, a medical apparatus provided with a medical instrument that carries out laparoscopic surgery will be described as an example.

First Embodiment

Figure 2:
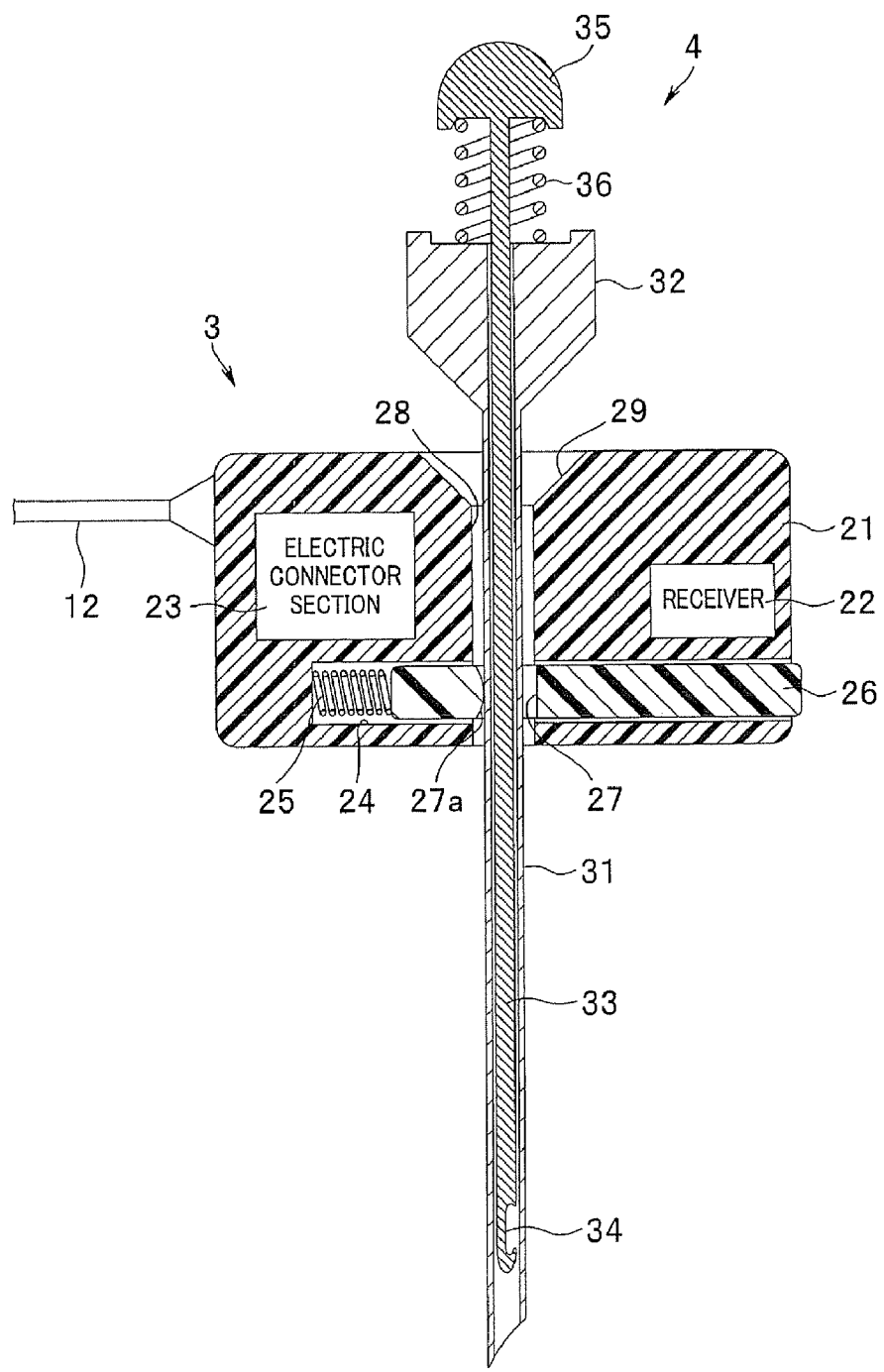
FIG. 2 is a cross-sectional view illustrating a configuration of an outside apparatus and a puncture needle according to the first embodiment of the present invention.
Figure 3:
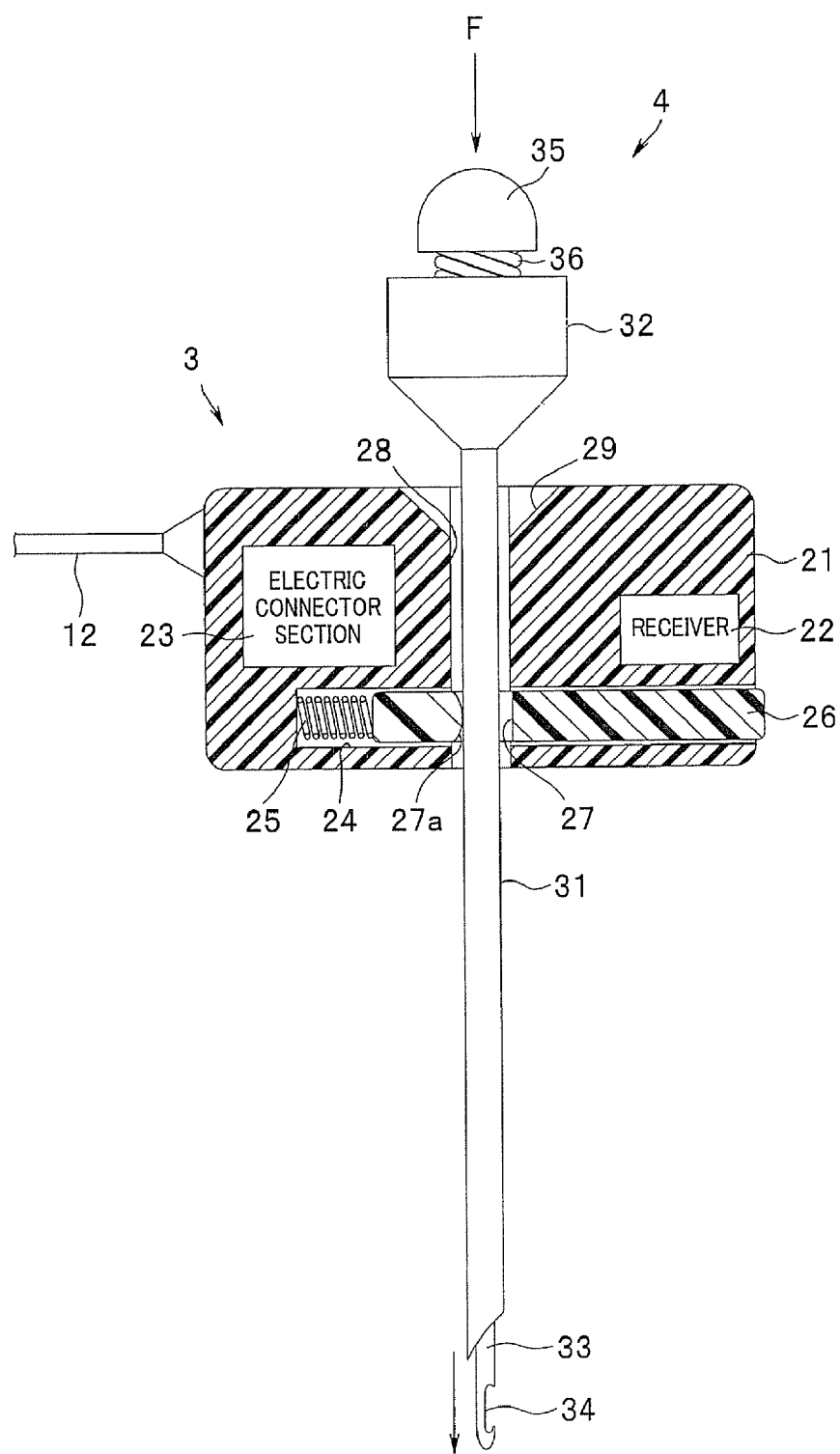
FIG. 3 is a partial cross-sectional view illustrating the operation of the puncture needle of the outside apparatus according to the first embodiment of the present invention.
Figure 4:
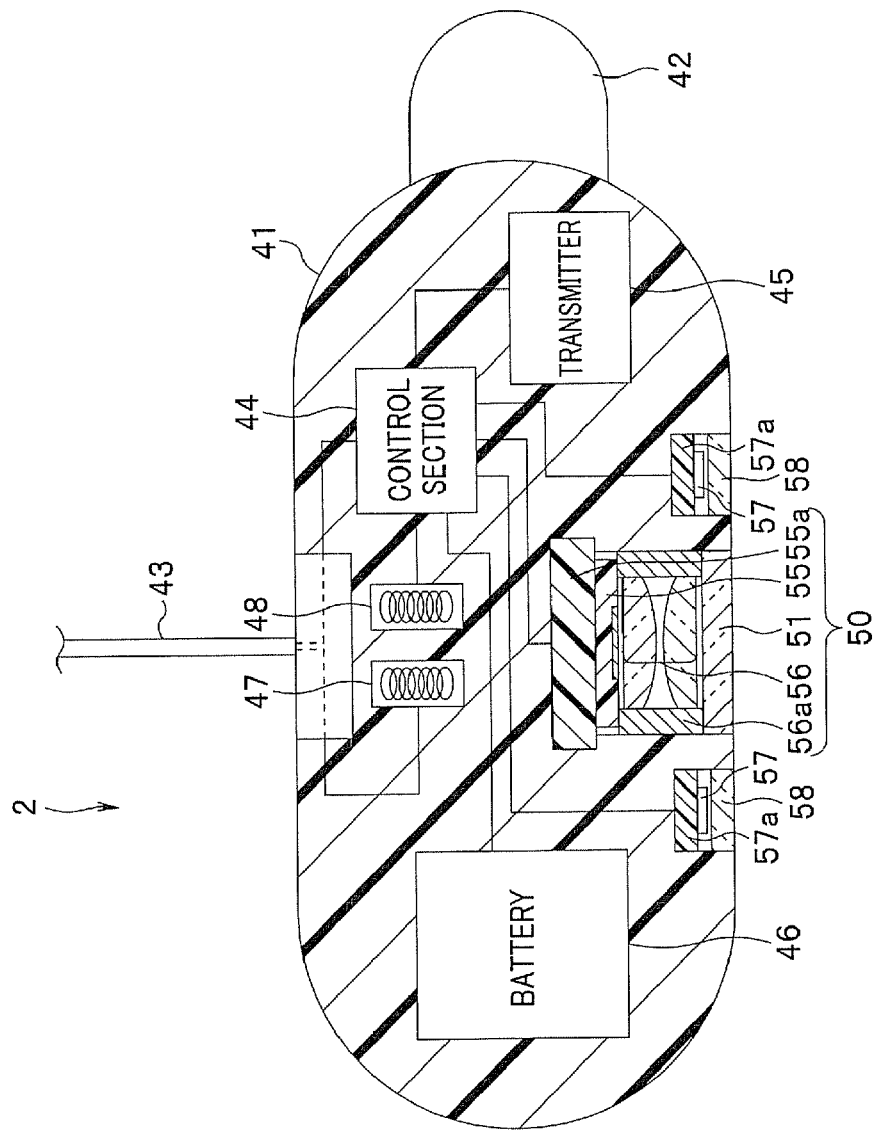
FIG. 4 is a cross-sectional view illustrating a configuration of a camera set up in the abdominal cavity according to the first embodiment of the present invention.
Figure 5:
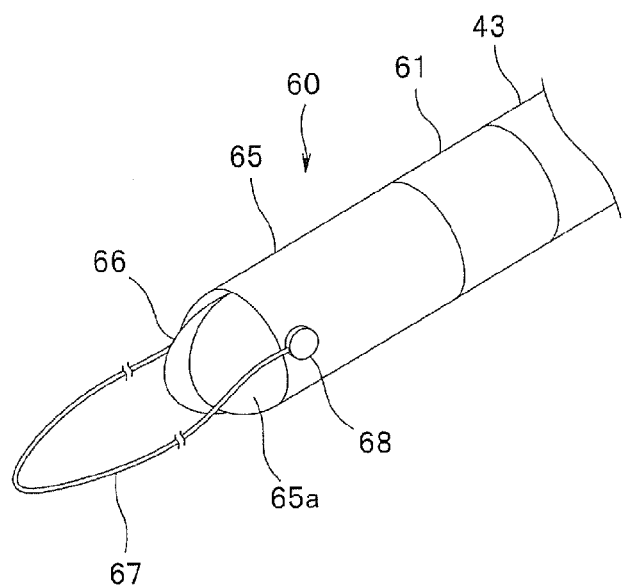
FIG. 5 is a perspective view illustrating a configuration of an end of an electric cable wire fitted with a drip-proof cap that covers the electric terminal section according to the first embodiment of the present invention.
Figure 6:
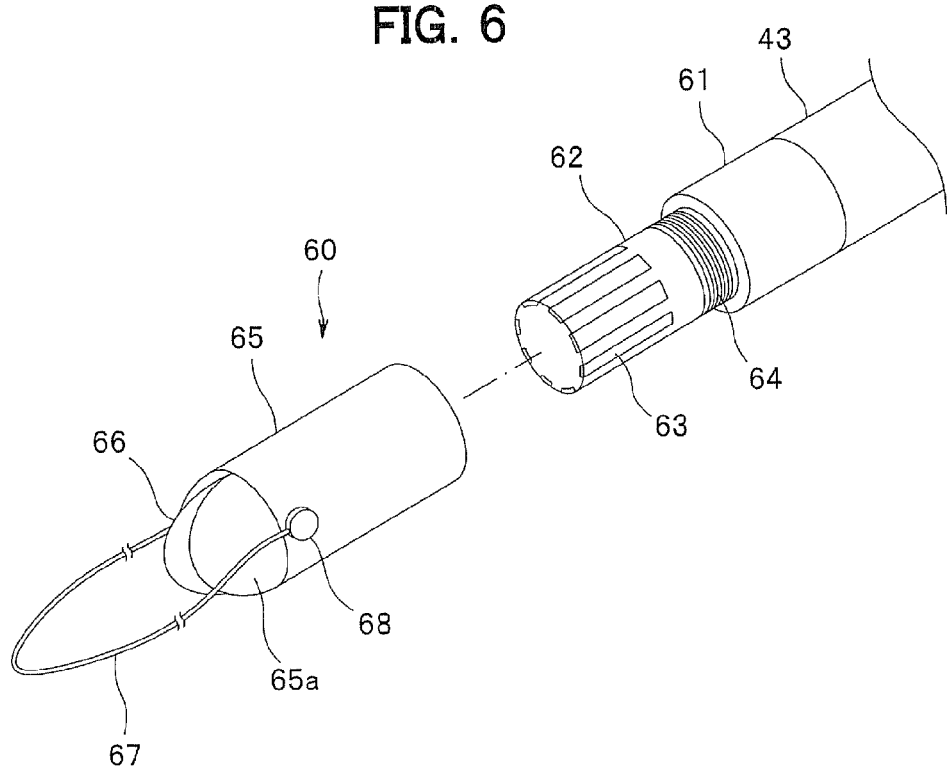
FIG. 6 is a perspective view showing the drip-proof cap detached from the electric terminal section according to the first embodiment of the present invention.
Figure 7:
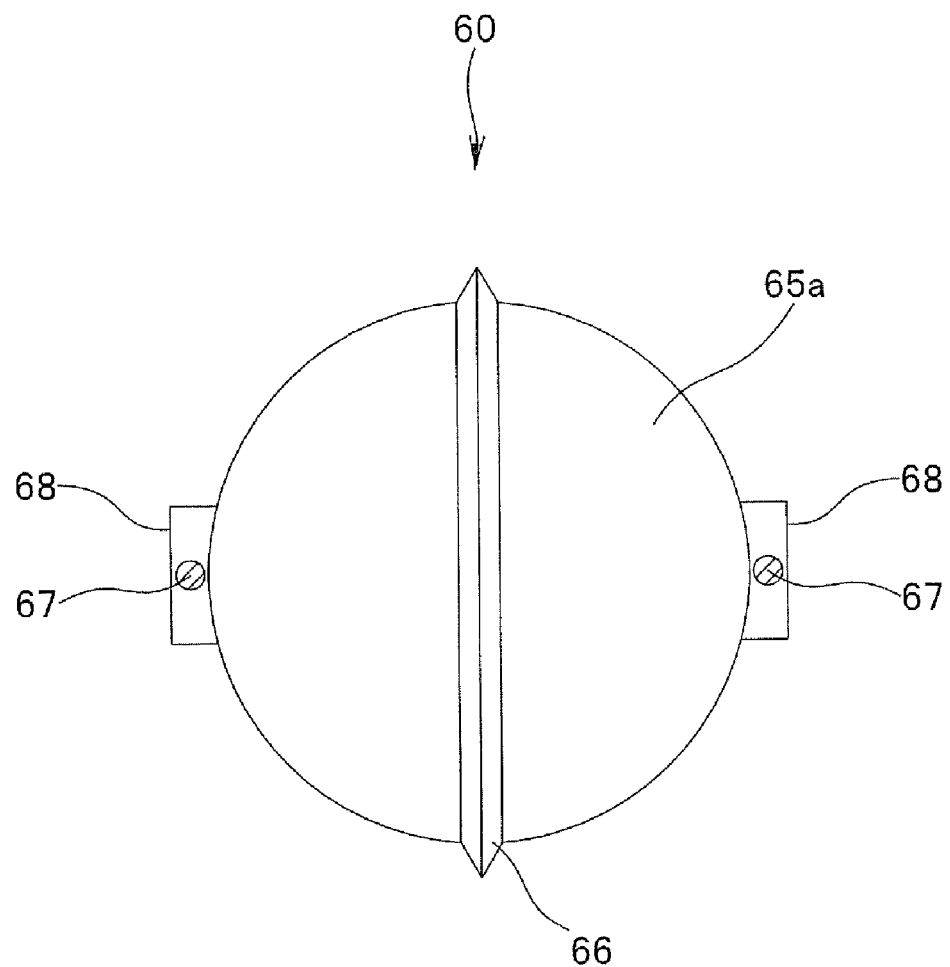
FIG. 7 is a front view illustrating a configuration of the drip-proof cap according to the first embodiment of the present invention.
Figure 8:
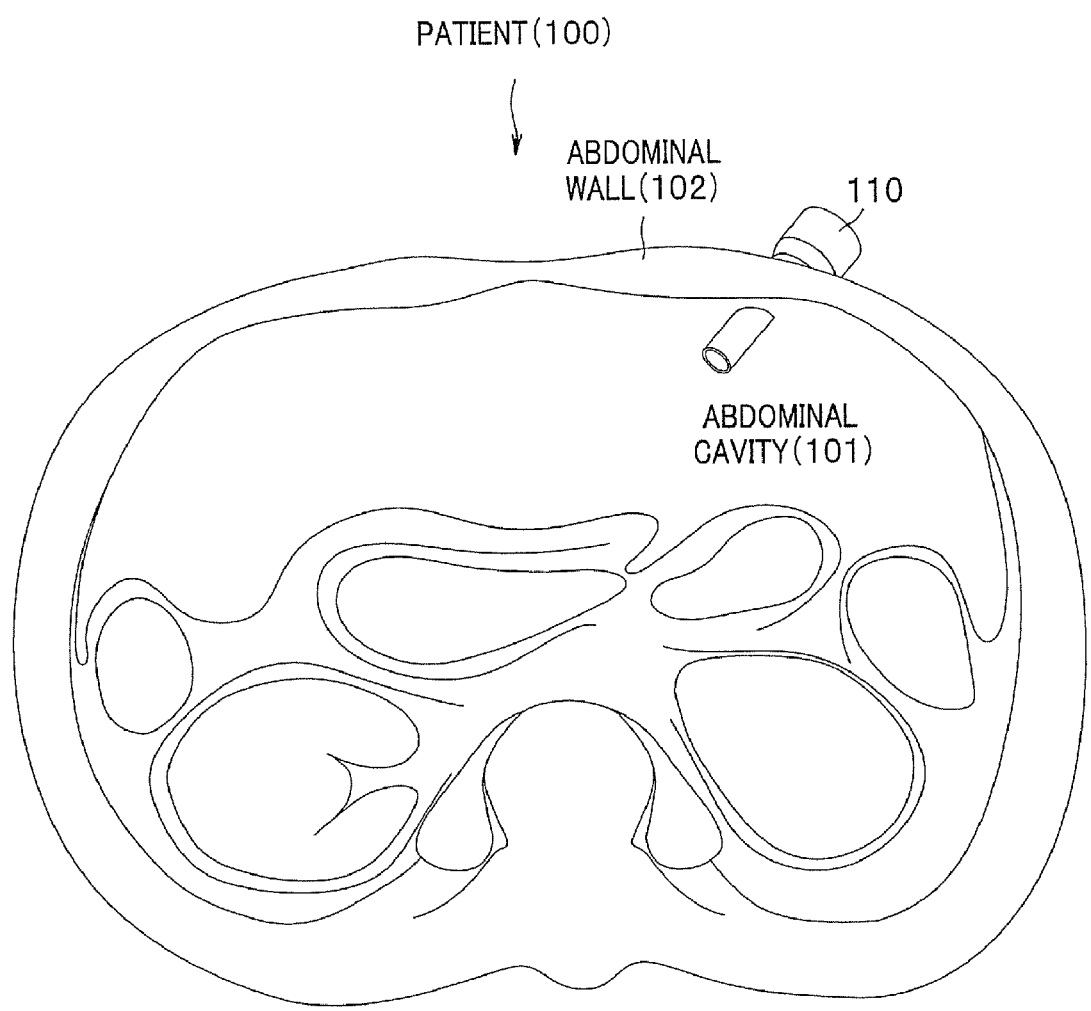
FIG. 8 is a diagram illustrating a trocar punctured into the abdominal wall of a patient according to the first embodiment of the present invention.
Figure 9:
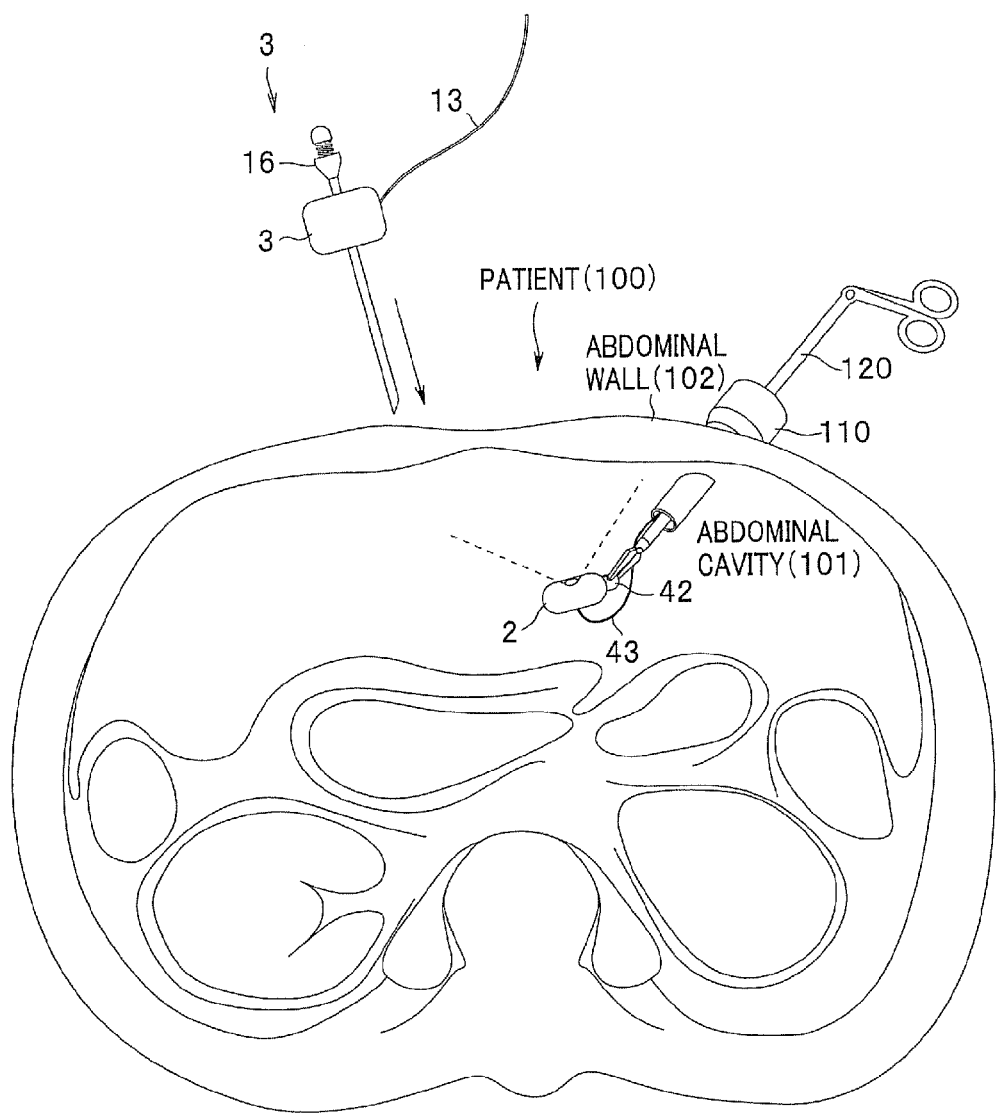
FIG. 9 is a diagram illustrating a procedure for introducing the camera set up in the abdominal cavity into the abdominal cavity according to the first embodiment of the present invention.
Figure 10:
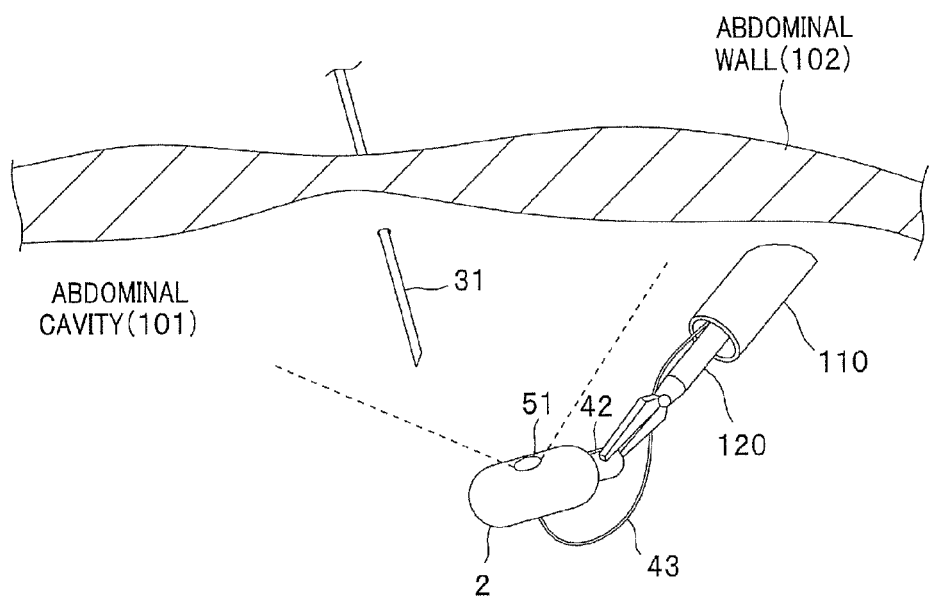
FIG. 10 is a diagram illustrating the hook needle punctured into the abdominal wall and illustrating a procedure for leaving the camera set up in the abdominal cavity indwelling in the abdominal cavity according to the first embodiment of the present invention.
Figure 11:
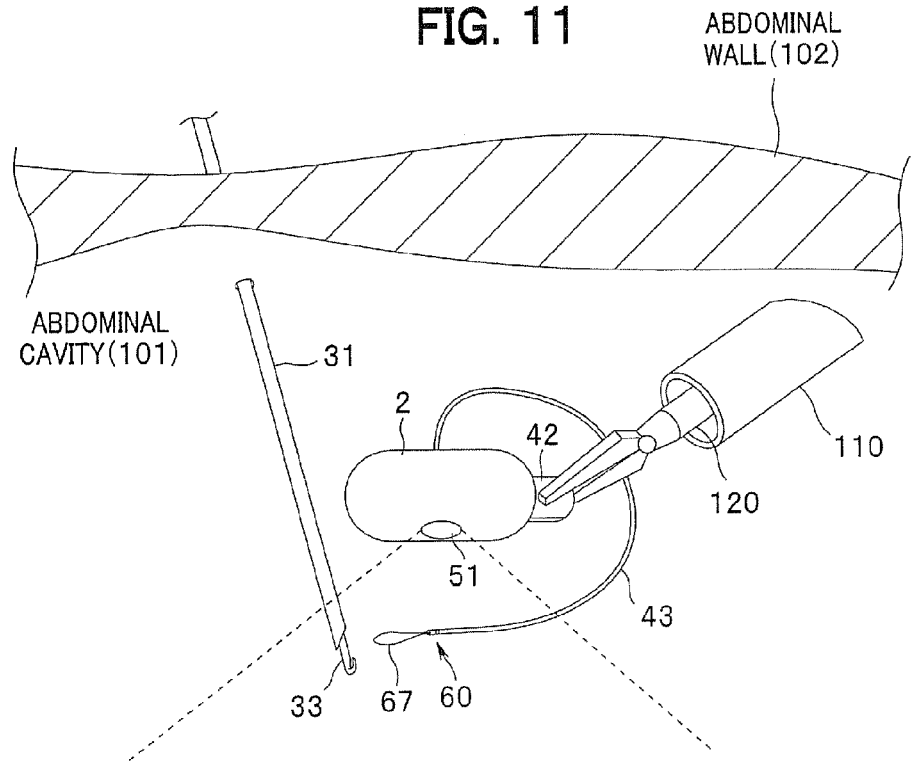
FIG. 11 is a diagram illustrating a state before the wire of the drip-proof cap is hooked by the hook needle and illustrating a procedure for leaving the camera set up in the abdominal cavity indwelling in the abdominal cavity according to the first embodiment of the present invention.
Figure 12:
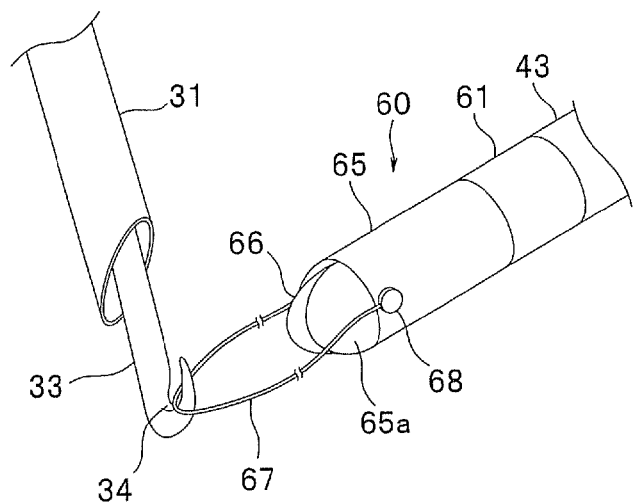
FIG. 12 is a diagram illustrating the wire of the drip-proof cap hooked by the hook needle and illustrating a procedure for introducing the camera set up in the abdominal cavity into the abdominal cavity according to the first embodiment of the present invention.
Figure 13:
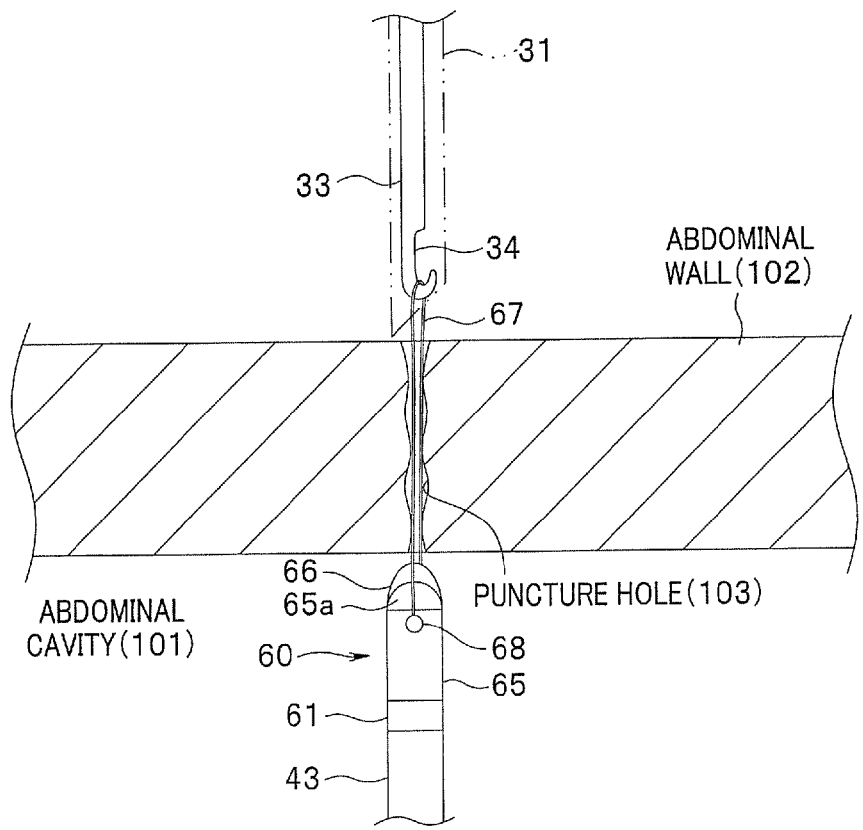
FIG. 13 is a diagram illustrating a state in which the electric cable wire of the camera set up in the abdominal cavity is lifted and illustrating a procedure for leaving the camera set up in the abdominal cavity indwelling in the abdominal wall according to the first embodiment of the present invention.
Figure 14:
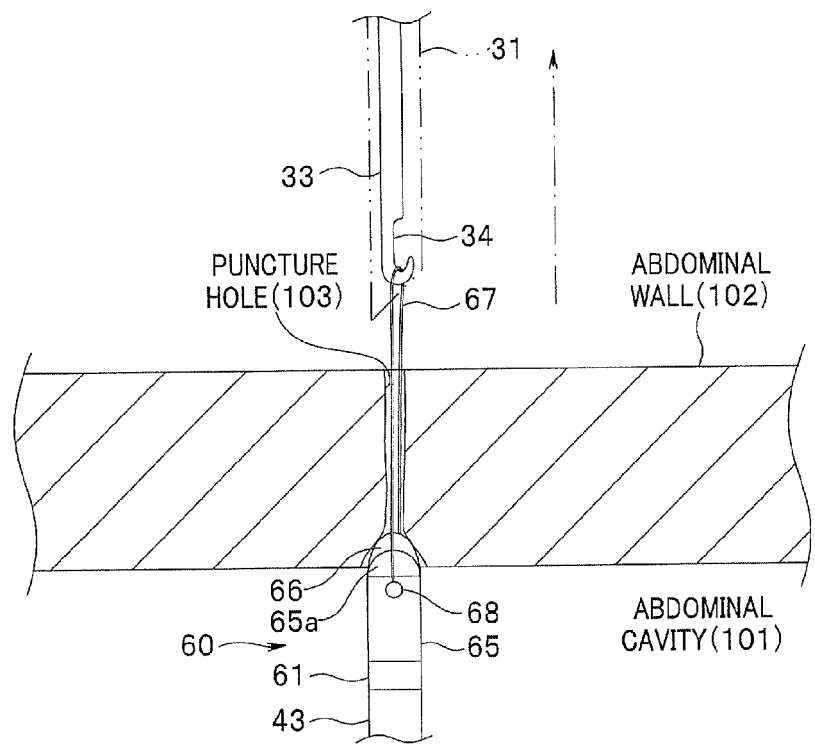
FIG. 14 is a diagram illustrating a state in which the edge of the drip-proof cap starts to dissect the abdominal wall and illustrating a procedure for leaving the camera set up in the abdominal cavity indwelling in the abdominal wall according to the first embodiment of the present invention.
Figure 15:
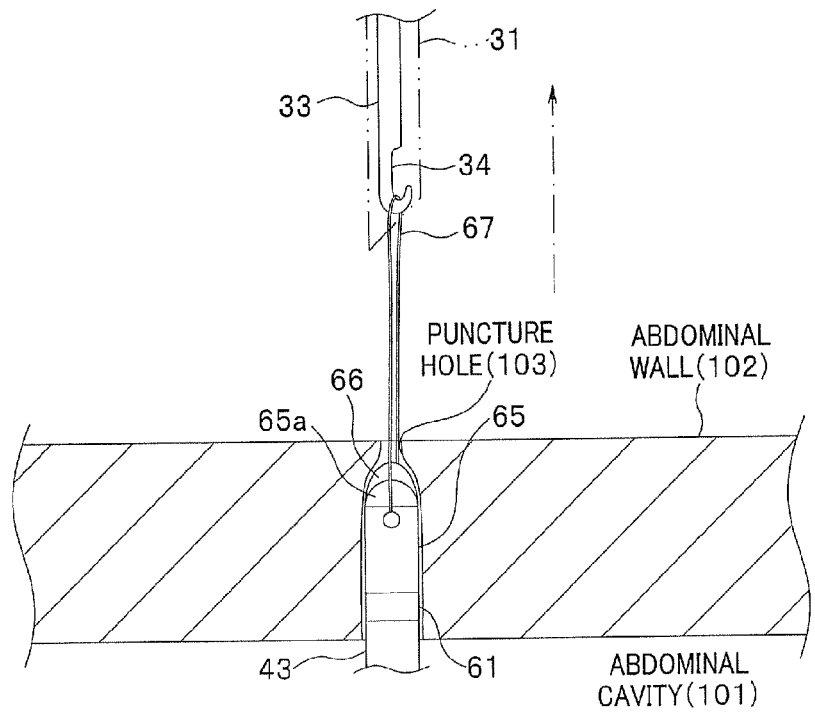
FIG. 15 is a diagram illustrating a state in which the edge of the drip-proof cap is dissecting the abdominal wall and illustrating a procedure for leaving the camera set up in the abdominal cavity indwelling in the abdominal wall according to the first embodiment of the present invention.
Figure 16:
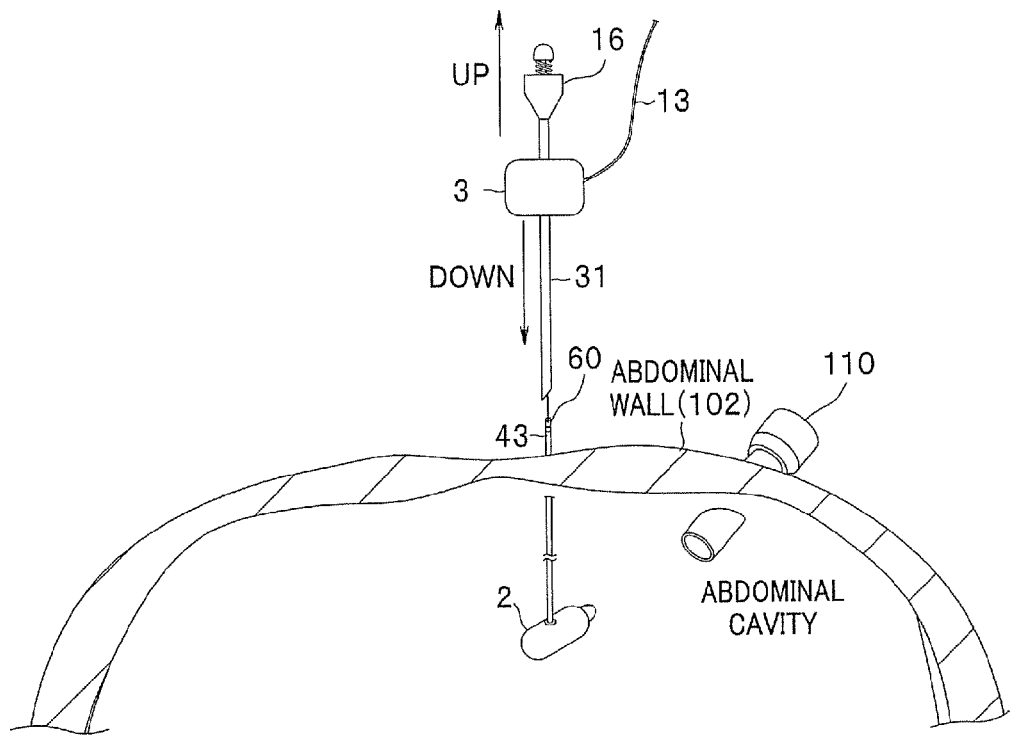
FIG. 16 is a diagram illustrating a state in which the hook needle is lifted and the outside apparatus is lowered along the hook needle and illustrating a procedure for leaving the camera set up in the abdominal cavity indwelling in the abdominal wall according to the first embodiment of the present invention.
Figure 17:
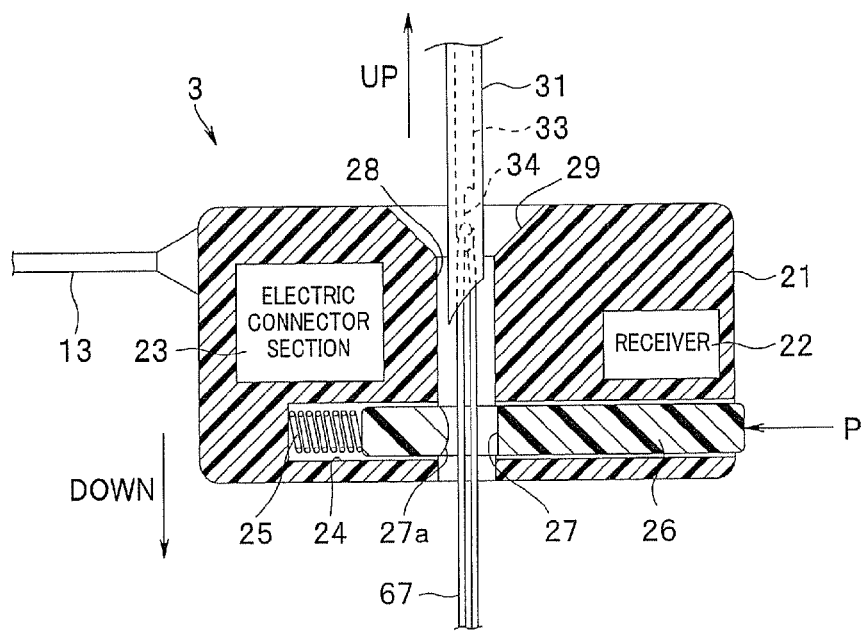
FIG. 17 is a cross-sectional view illustrating the operation of the outside apparatus according to the first embodiment of the present invention.
Figure 18:
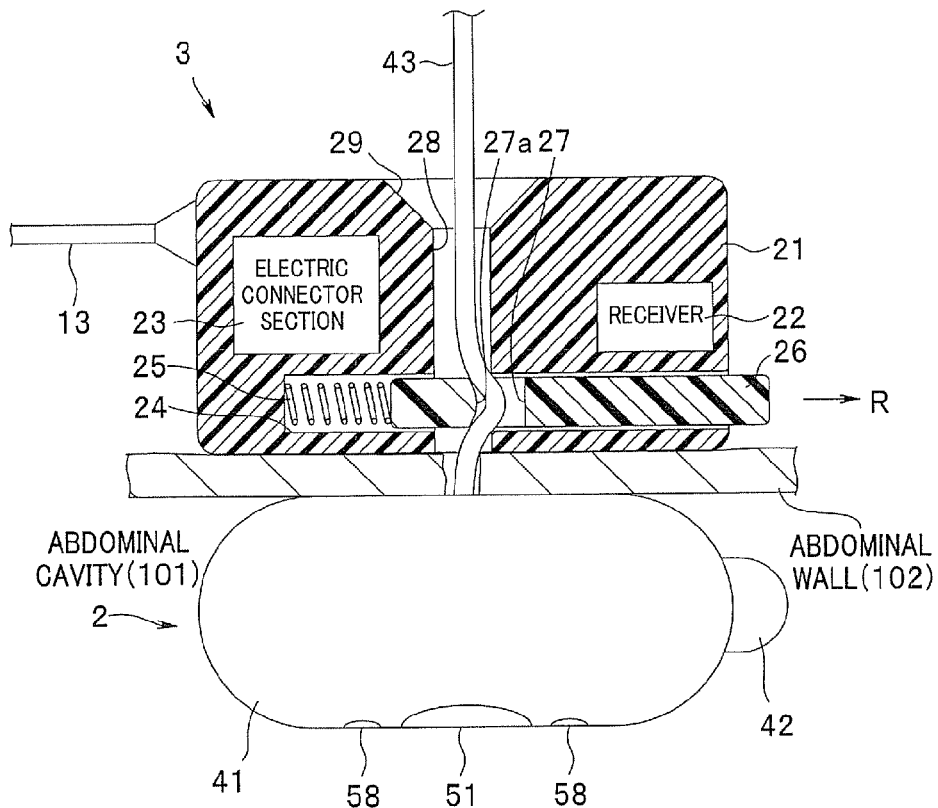
FIG. 18 is a cross-sectional view of the outside apparatus and the camera set up in the abdominal cavity according to the first embodiment of the present invention when the outside apparatus is placed on the abdomen.
Figure 19:
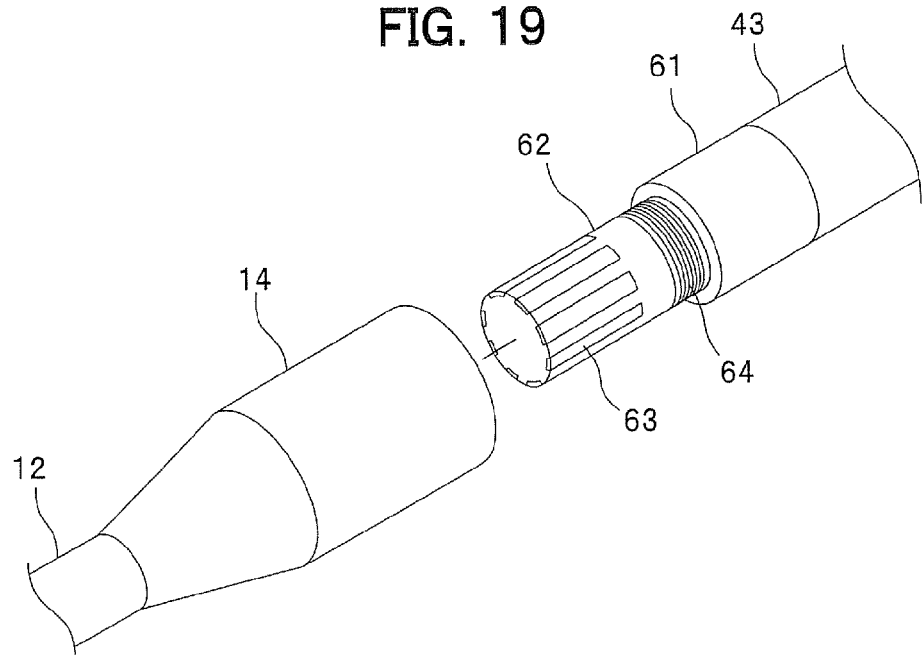
FIG. 19 is a perspective view illustrating a state in which the electric terminal section is connected to the connector of the communication cable according to the first embodiment of the present invention.
Figure 20:
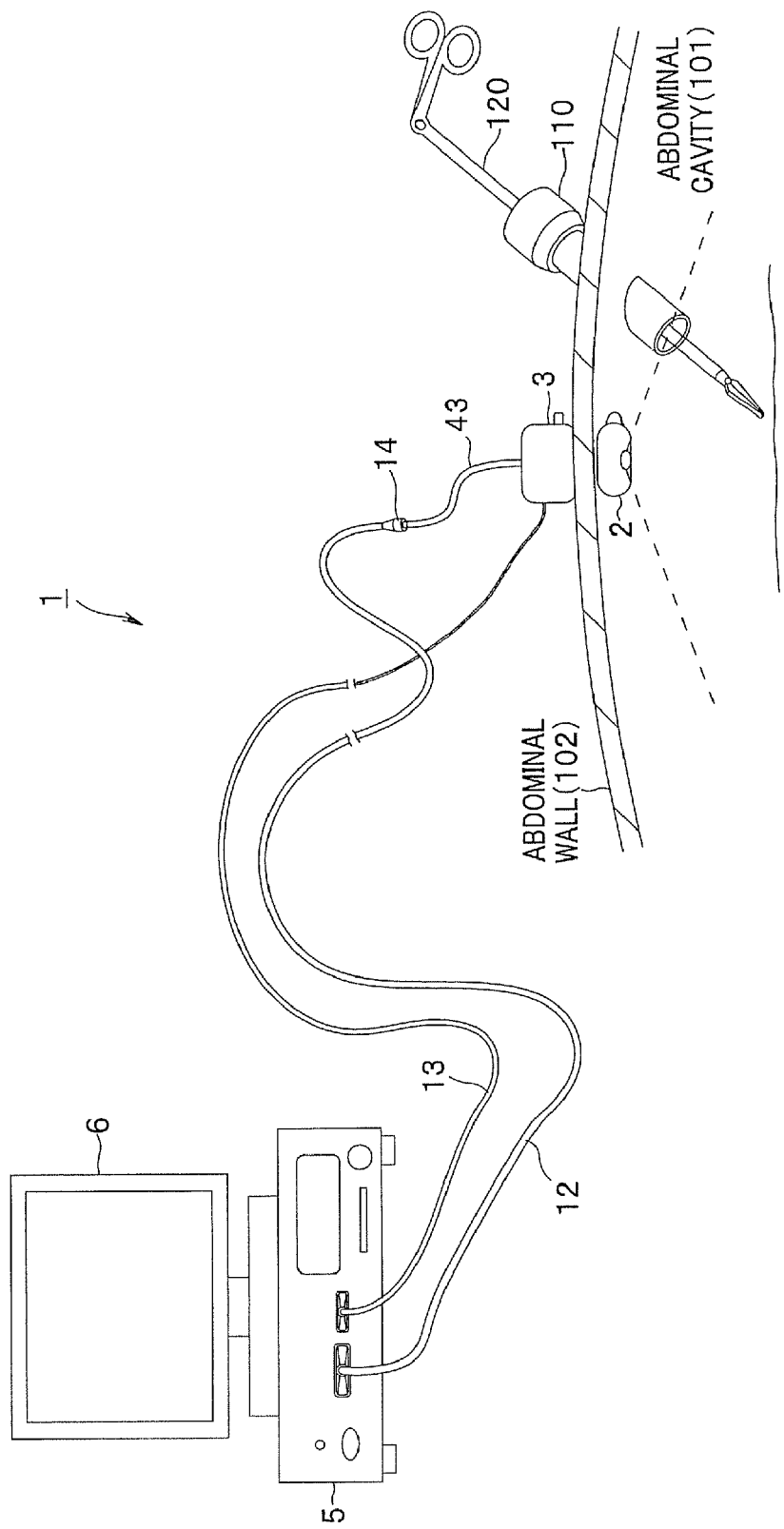
FIG. 20 is an overall configuration diagram of the endoscope system illustrating a state in which camera set up in the abdominal cavity is left indwelling on the abdominal wall according to the first embodiment of the present invention.

First, an endoscope system which is a medical system of the present invention used for laparoscopic surgery will be described. FIG. 1 to FIG. 20 are related to a first embodiment of the present invention, FIG. 1 is a diagram illustrating a configuration of an endoscope system which is a medical apparatus, FIG. 2 is a cross-sectional view illustrating a configuration of an outside apparatus and a puncture needle, FIG. 3 is a partial cross-sectional view illustrating the operation of the puncture needle of the outside apparatus, FIG. 4 is a cross-sectional view illustrating a configuration of a camera set up in the abdominal cavity, FIG. 5 is a perspective view illustrating a configuration of an end of an electric cable wire fitted with a drip-proof cap that covers the electric terminal section, FIG. 6 is a perspective view showing the drip-proof cap detached from the electric terminal section, FIG. 7 is a front view illustrating a configuration of the drip-proof cap, FIG. 8 is a diagram illustrating a trocar punctured into the abdominal wall of a patient, FIG. 9 is a diagram illustrating a procedure for introducing the camera set up in the abdominal cavity into the abdominal cavity, FIG. 10 is a diagram illustrating the hook needle punctured into the abdominal wall and illustrating a procedure for leaving the camera set up in the abdominal cavity indwelling in the abdominal cavity, FIG. 11 is a diagram illustrating a state before the wire of the drip-proof cap is hooked by the hook needle and illustrating a procedure for leaving the camera set up in the abdominal cavity indwelling in the abdominal cavity, FIG. 12 is a diagram illustrating the wire of the drip-proof cap hooked by the hook needle and illustrating a procedure for introducing the camera set up in the abdominal cavity into the abdominal cavity, FIG. 13 is a diagram illustrating a state in which the electric cable wire of the camera set up in the abdominal cavity is lifted and illustrating a procedure for leaving the camera set up in the abdominal cavity indwelling in the abdominal wall, FIG. 14 is a diagram illustrating a state in which the edge of the drip-proof cap starts to dissect the abdominal wall and illustrating a procedure for leaving the camera set up in the abdominal cavity indwelling in the abdominal wall, FIG. 15 is a diagram illustrating a state in which the edge of the drip-proof cap is dissecting the abdominal wall and illustrating a procedure for leaving the camera set up in the abdominal cavity indwelling in the abdominal wall, FIG. 16 is a diagram illustrating a state in which the hook needle is lifted and the outside apparatus is lowered along the hook needle and illustrating a procedure for leaving the camera set up in the abdominal cavity indwelling in the abdominal wall, FIG. 17 is a cross-sectional view illustrating the operation of the outside apparatus, FIG. 18 is a cross-sectional view of the outside apparatus and the camera set up in the abdominal cavity when the outside apparatus is placed on the abdomen, FIG. 19 is a perspective view illustrating a state in which the electric terminal section is connected to the connector of the communication cable and FIG. 20 is an overall configuration diagram of the endoscope system illustrating a state in which camera set up in the abdominal cavity is left indwelling on the abdominal wall.

Figure 1:
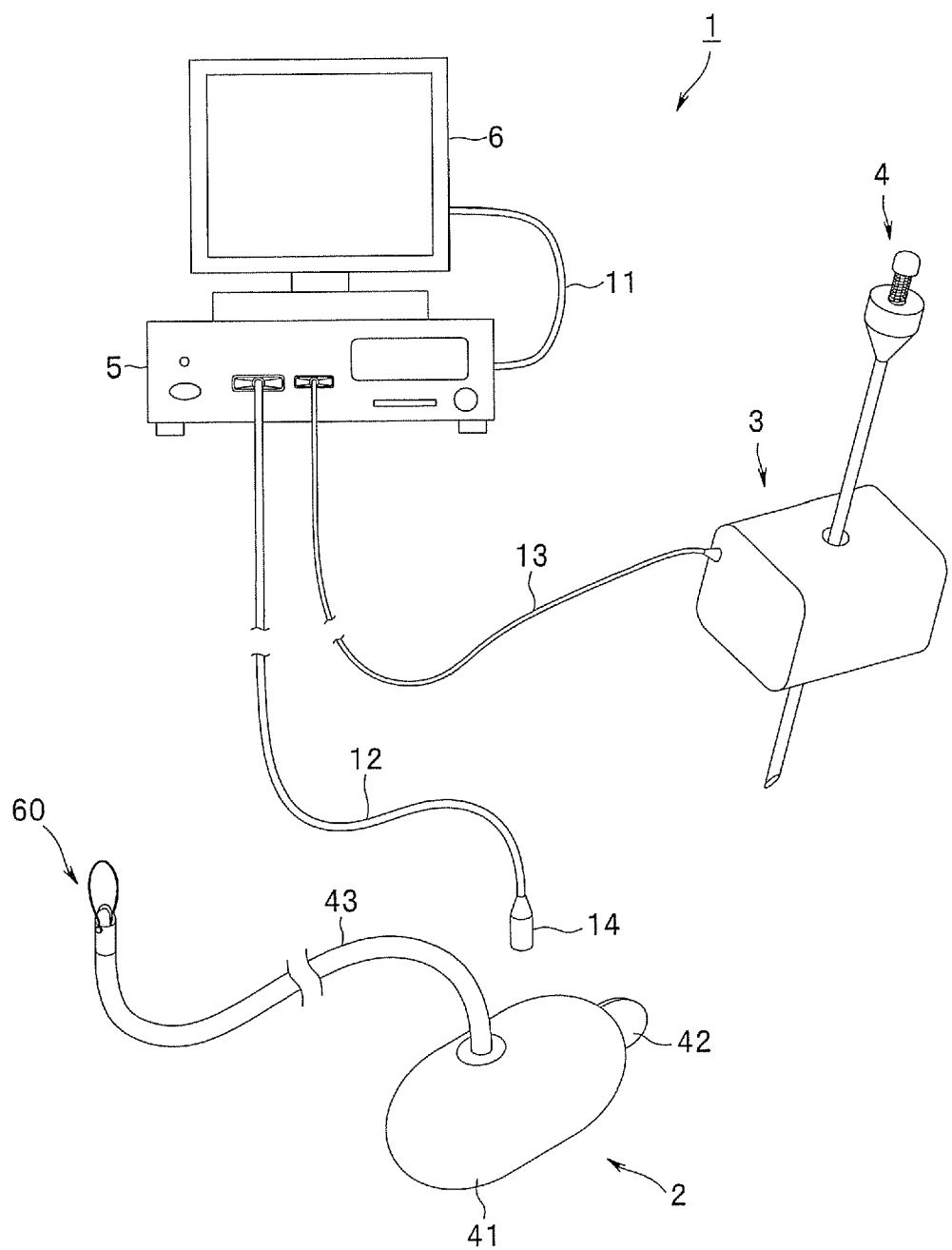
FIG. 1 is related to a first embodiment of the present invention and is a diagram illustrating a configuration of an endoscope system, which is a medical apparatus.

As shown in FIG. 1, an endoscope system 1 of the present embodiment that performs laparoscopic surgery is mainly configured by including a camera set up in the abdominal cavity (hereinafter, abbreviated as "camera") 2 which is a small capsule type medical apparatus, an outside apparatus 3 which is a camera fixing unit for fixing and holding the camera 2 introduced into the body from outside the body, a hook needle 4 of puncturing means which is a puncture needle freely inserted/removed into/from the outside apparatus 3 for hooking and lifting the camera 2, a camera control unit (hereinafter, abbreviated as "CCU") 5 which is a signal processing apparatus with a built-in image processing circuit and a monitor 6 which is a display apparatus electrically connected with the CCU 5 via a cable 11 for displaying an observed image.

The CCU 5 is detachably connected with a communication cable 12 which is electrically connected with the camera 2 via an electric connector, generates an image signal transmitted from the camera 2 electrically connected with the communication cable 12 as a video signal and outputs the video signal to the monitor 6. The monitor 6 is, for example, a liquid crystal display, receives a video signal outputted from the CCU 5 and displays an observed image by the camera 2 on a screen. Furthermore, the CCU 5 is detachably connected to the outside apparatus 3 via an electric cable 13.

Next, the outside apparatus 3 and the hook needle 4 will be described in detail using FIG. 2 and FIG. 3 below.

As shown in FIG. 2 and FIG. 3, the outside apparatus 3 is a camera fixing unit that pulls and fixes the camera 2 in the body cavity, and a casing 21 thereof incorporates a receiver 22 and an electric connector section 23 electrically connected to the receiver 22.

The electric connector section 23 is connected to an electric cable 13 connected to the CCU 5. The outside apparatus 3 transmits power from the CCU 5 and a signal from the receiver 22 to the CCU 5 via the electric cable 13.

A slide hole 24 is formed in the casing 21 in the horizontal direction from one side. A fixing lever 26 constituting a fixing unit made of a non-magnetic substance, to an end face of which a biasing spring 25 is fixed, is inserted in the slide hole 24. The fixing lever 26 has a rectangular-parallelepiped-like shape and is disposed slidably along the slide hole 24 toward the inside of the casing 21. Furthermore, a hole section 27 having an arc-shaped surface 27a, which is convex with respect to the biasing spring 25, is formed at some midpoint of the fixing lever 26.

An insertion portion 28 that vertically penetrates the casing 21 is formed in the casing 21. A conical tapered surface 29 that spreads toward the top which becomes an opening on the top surface of the casing 21 is formed in the insertion portion 28.

In the outside apparatus 3 configured as shown above, the hook needle 4 is inserted into the vertically penetrating hole so as to be freely inserted or extracted at a slide position at which the fixing lever 26 is pushed into the casing 21 in such a way that the hole section 27 of the fixing lever 26 coincides with the insertion portion 28.

The hook needle 4 which can be freely inserted into the outside apparatus 3 is configured by including a cylindrical puncture needle tube 31, a needle head 32 disposed connected to the upper part of the puncture needle tube 31, a puncturing rod 33, at a distal end of which a hook section 34 that is slidably inserted in the puncture needle tube 31 is formed, a hook head 35 disposed connected to the upper part of the puncturing rod 33, and a spring 36 interposed between the hook head 35 and the needle head 32.

The puncture needle tube 31 is a long metal tube of approximately 3 mm in diameter having a sharp needle shape whose distal end is diagonally cut. The needle head 32 is greater in outer diameter than the puncture needle tube 31 and the distal end side thereof is formed into a conic shape and formed as one piece with the puncture needle tube 31. The needle head 32 is configured to come into contact with the tapered surface 29 formed at the top of the casing 21 so as to prevent the hook needle 4 from falling downward off the casing 21.

The puncturing rod 33 is an elongated metal bar and the hook head 35 disposed connected to the upper part thereof is biased by the spring 36 in a direction in which the hook head 35 moves away from the needle head 32. This causes the hook section 34 formed at the distal end of the puncturing rod 33 to be accommodated in the puncture needle tube 31.

Furthermore, when the user pushes the hook head 35 into the puncture needle tube 31 against the biasing force of the spring 36 (arrow F in FIG. 3), the hook section 34 formed at the distal end of the hook needle 4 juts out of the distal end of the puncture needle tube 31.

When the hook needle 4 configured as shown above is inserted in the insertion portion 28 of the casing 21 and the hole section 27 of the wire fixing lever 26, the fixing lever 26 is inserted in the casing 21 and fixed thereto under a pressure toward the outside of the casing 21 by the biasing force of the biasing spring 25. That is, the hook needle 4 is fixed by being inserted in the casing 21 in a condition in which the outer circumferential surface of the puncture needle tube 31 is pressed by the arc-shaped surface 27a formed on one side of the hole section 27 of the fixing lever 26 and comes into contact with the inner surface of the insertion portion 28.

Next, the camera 2 will be explained in detail using FIG. 4 below.

As shown in FIG. 4, the camera 2 is provided with an outer enclosure section 41 which constitutes a capsule-like casing section, a tabular grasping portion 42 that protrudes from one side section of the outer enclosure section 41 and a communication cable wire 43 which is communication means that extends from the top center of the outer enclosure section 41.

The outer enclosure section 41, together with a control section 44, a transmitter 45, a battery 46, and two electromagnetic coils 47 and 48, constitutes a camera unit which is an image pickup section and incorporates an image pickup unit 50 which is image pickup means, and a plurality of illumination sections 57 made up of and LED, an organic EL or the like serving as a light source of illumination light which constitute a small and low power consumption illumination unit.

The control section 44 is electrically connected to the transmitter 45, the image pickup unit 50 and the illumination section 57. Furthermore, to drive/control each component, the control section 44 receives a drive power supply via the battery 46 or the communication cable wire 43. Furthermore, the control section 44 is also electrically connected to one electromagnetic coil 48. One of wires inserted in the communication cable wire 43 is connected to the other electromagnetic coil 47.

The image pickup unit 50 is mainly configured by including a solid image pickup device 55 such as a CCD or a CMOS, an image pickup device drive circuit section 55a that drives/controls the solid image pickup device 55 and photoelectrically converts photographing light impinged on the solid image pickup device 55, an objective lens group 56 that condenses photographing light to the solid image pickup device 55 and a lens holding frame 56a that holds the objective lens group 56. For the image pickup unit 50 of the present embodiment, an image pickup optical system that picks up images of a wide-angle field of view is set such that the angle of view that allows photographing becomes for example 120° or more. Furthermore, the image pickup unit 50 may also have a zoom function or the like.

The illumination section 57 is disposed on an illumination drive circuit section 57a whereby the illumination section 57 is driven/controlled. The outer enclosure section 41 is provided with cover members 51 and 58 made of sapphire glass or the like constituting a transparent observation window and an illumination window that hermetically cover the image pickup unit 50 and each illumination section 57. The cover members 51 and 58 are disposed at the bottom section of the outer enclosure section 41.

In the camera 2, when power is supplied to the communication cable wire 43, a current is supplied to the electromagnetic coil 47 and the magnetic force generated by the electromagnetic coil 47 causes an induced current to be generated in the other electromagnetic coil 48, which is then inputted to the control section 44. The control section 44 incorporates a changeover switch (not shown) and is configured to change, when the induced current is inputted from the electromagnetic coil 48, the internal switch so as to switch the power supply from the battery 46 to a power supply via the communication cable wire 43.

The communication cable wire 43 is a communication cable to exchange various instruction signals to the control section 44 in the camera 2 and image pickup signals or the like from the image pickup unit 50 with the CCU 5.

Next, an electric terminal section provided at an extending end of the communication cable wire 43 that extends from the outer enclosure section 41 of the camera 2 and a cover member that covers the electric terminal section will be described in detail using FIG. 5 to FIG. 7 below.

As shown in FIG. 5 and FIG. 6, an electric terminal section 61 which is electric connection means is provided at the extending end of the communication cable wire 43. The electric terminal section 61 is a male connector having a columnar male terminal 62 formed so as to have a smaller outside diameter on the distal end side thereof. The male terminal 62 is configured to be electrically connectable to a female connector 14 (see FIG. 1) provided at an end section of the communication cable 12 connected to the CCU 5.

Furthermore, the male terminal 62 of the electric terminal section 61 is provided with a plurality of electric contacts 63 in the circumferential direction of the outer circumferential portion and a screw groove 64 is formed at the root portion thereof. A drip-proof cap 60 which is drip-proof means is fitted to the electric terminal section 61 so as to cover the male terminal 62. Fitted and covered with the drip-proof cap 60, the male terminal 62 is protected against drips (and dust).

The drip-proof cap 60 has a quasi-cylindrical cover body 65 and a distal end face 65a formed into a semispherical shape so as to close the distal end of the cover body 65. As shown in FIG. 5 to FIG. 7, the distal end face 65a is provided with an edge 66 of dissection means constituting a dissection section which is a blade-shaped member for tissue dissection.

The edge 66 is disposed rectilinearly so as to pass through the center section of the surface of the distal end face 65a and formed in an arc shape along the surface shape of the distal end face 65a in a side view. Furthermore, the drip-proof cap 60 is provided with a wire 67 of locking means which is a loop-shaped locking section extending from the side periphery section to the front of the cover body 65.

The cover body 65 is further provided with two fixing sections 68 that fix the end sections of the wire 67 at two locations of the outer circumferential portion. The wire 67 is formed of a metal wire such as one used for snare forceps of an endoscope treatment instrument and a non-metallic elastic ring or the like.

When the cover body 65 is screwed to the screw groove 64 formed at the root portion of the male terminal 62, the drip-proof cap 60 is thereby fitted to the electric terminal section 61, which prevents the drip-proof cap 60 from dropping off from the electric terminal section 61. The configuration of preventing the drip-proof cap 60 from dropping off from the electric terminal section 61 is not limited to fastening with a screw, but such a configuration may also be adopted that the electric terminal section 61 or (and) the cover body 65 is provided with a magnet so that attraction by the magnetic force prevents the drip-proof cap 60 from dropping off from the electric terminal section 61.

The endoscope system 1 of the present embodiment configured as shown above is used for surgical operation under a laparoscope and used for medical treatment inside the abdominal cavity, one of body cavities of the patient.

Here, the procedure and operation for setting up the camera 2 of the endoscope system 1 of the present embodiment in the abdominal cavity, which is the body cavity of the patient, for surgical operation under a laparoscope will be described in detail below using FIG. 8 to FIG. 20.

First, the operator performs dissecting a small dissection section in the abdominal wall 102 of a patient 100 using a scalpel or the like and punctures a trocar 110 into the dissected section as shown in FIG. 8.

The operator inserts the puncture needle tube 31 of the hook needle 4 into the insertion portion 28 provided in the outside apparatus 3 as shown in FIG. 2 and FIG. 3. In this case, the operator pushes the fixing lever 26 into the casing 21 so that the puncture needle tube 31 penetrates the outside apparatus 3 and inserts the puncture needle tube 31 so as to penetrate the hole section 27 of the fixing lever 26. In the outside apparatus 3, the electric connector of the electric cable 13 is connected to the CCU 5.

The operator moves the outside apparatus 3 to a position sufficiently close to the needle head 32 located at the root side of the puncture needle tube 31, and causes the puncture needle tube 31 to sufficiently stick out of the underside of the outside apparatus 3 (see FIG. 2 and FIG. 3). In this condition, the outside apparatus 3 is designed not to fall off from the puncture needle tube 31 with the arc-shaped surface 27a, which is one wall surface of the hole section 27 of the fixing lever 26, contacting and holding the puncture needle tube 31 by means of the biasing force of the biasing spring 25.

Next, the operator grasps the grasping portion 42 of the camera 2 using a treatment instrument 120 such as grasping forceps and introduces the camera 2 into the abdominal cavity 101 via the trocar 110 punctured through the abdominal wall 102. The operator fits the drip-proof cap 60 to the electric terminal section 61 of the communication cable wire 43 of the camera 2 beforehand.

After introducing the camera 2 into the abdominal cavity 101, the operator directs the observation direction of the camera 2 so as to be able to take images of the wall surface direction of the abdominal wall 102 in the abdominal cavity 101 as shown in FIG. 9 and FIG. 10. Next, the operator punctures the puncture needle tube 31 of the hook needle 4 which is inserted and held in the outside apparatus 3 so as to penetrate the abdominal wall 102 while checking the photographing image from the camera 2 with the monitor 6. The camera 2 in this case is driven by the power from the battery 46 and an image signal picked up by the image pickup unit 50 is wirelessly communicated from the transmitter 45 to the receiver 22 of the outside apparatus 3.

To lead the puncturing rod 33 out of the puncture needle tube 31, the operator pushes in the hook head 35 (see FIG. 3). In this case, as shown in FIG. 11, the operator changes the observation direction of the camera 2 and checks the position of the wire 67 of the drip-proof cap 60 attached to the end section of the communication cable wire 43. FIG. 11 illustrates a state in which the camera 2 photographing in the upward direction which is the direction of the abdominal wall 102 is turned upside down so as to take images in the downward direction.

While checking the observed image of the camera 2 displayed on the monitor 6, the operator hooks the hook section 34 formed on the puncturing rod 33 onto the wire 67 of the drip-proof cap 60 as shown in FIG. 12. When the wire 67 of the drip-proof cap 60 is hooked onto the hook section 34, the operator stops pushing the hook head 35 of the puncturing rod 33. The puncturing rod 33 is then pulled into the puncture needle tube 31 with the wire 67 hooked onto the hook section 34.

Next, the operator pulls the puncture needle tube 31 of the hook needle 4 out of the abdominal cavity 101 with the wire 67 of the drip-proof cap 60 hooked onto the hook section 34 of the puncturing rod 33 as shown in FIG. 13. Furthermore, the operator further pulls the hook needle 4 so that the communication cable wire 43 fitted with the drip-proof cap 60 penetrates the abdominal wall 102 and goes out of the body.

After reaching the wall surface of the abdominal wall 102, the drip-proof cap 60 passes through the puncturing hole 103 of the abdominal wall 102 formed through puncturing by the hook needle 4 with the edge 66 dissecting the tissue of the abdominal wall 102 as shown in FIG. 14 and FIG. 15. Thus, the operator can easily pull the drip-proof cap 60 out of the abdominal wall 102 without being caught in the abdominal wall 102. When pulling the drip-proof cap 60 and the communication cable wire 43 fitted with the drip-proof cap 60 out of the abdominal cavity 101 via the puncturing hole 103, the operator thereby easily allows the drip-proof cap 60 and the communication cable wire 43 to pass through the abdominal wall 102.

As shown in FIG. 16, the operator then pulls the communication cable wire 43, allows the outside apparatus 3 to move relative to the puncture needle tube 31 in the direction of the abdomen of the patient 100 (in the DOWN direction in the figure) and continues to pull the puncture needle tube 31 until the communication cable wire 43 fitted with the drip-proof cap 60 completely passes through the insertion portion 28 of the outside apparatus 3.

In this case, the operator pushes the fixing lever 26 of the outside apparatus 3 into the casing 21 (direction shown by an arrow P in FIG. 17), and can thereby easily cause the outside apparatus 3 to slide relative to the puncture needle tube 31 of the hook needle 4. When the communication cable wire 43 has passed through the insertion portion 28 of the outside apparatus 3, the operator then causes the outside apparatus 3 to move toward the abdomen of the patient 100, relative to the communication cable wire 43 this time while pulling the communication cable wire 43.

That is, the operator can easily cause the outside apparatus 3 to slide relative to the communication cable wire 43 by keeping the fixing lever 26 of the outside apparatus 3 pushed into the casing 21.

The operator then continues to pull the communication cable wire 43 until the outside apparatus 3 and the camera 2 come closer to each other to sandwich the abdominal wall 102 with the outside apparatus 3 placed on the top of the abdomen of the patient 100 as shown in FIG. 18. In this case, the operator causes the top of the camera 2 to come into close enough contact with the inner surface of the abdominal wall 102 and then stops pushing the fixing lever 26 of the outside apparatus 3.

The fixing lever 26 of the outside apparatus 3 then moves in the direction shown by an arrow R in FIG. 18 under the urging force of the biasing spring 25, where the hole section 27 is positioned deviated from the insertion portion 28 of the casing 21. The communication cable wire 43 inserted in the hole section 27 and insertion portion 28 remains caught therein and locked to the casing 21. In this case, the communication cable wire 43 is always held under a certain or higher level of tension. Thus, with the communication cable wire 43 being always kept under a certain level of tension or higher, the outside apparatus 3 and the camera 2 remain positioned close to each other sandwiching the abdominal wall 102 and the camera 2 is thereby fixed to the inner surface of the abdominal wall 102 in the abdominal cavity 101.

The operator then removes the drip-proof cap 60 attached to the end section of the communication cable wire 43 that has been pulled out. The operator then connects the electric terminal section 61 of the communication cable wire 43 to the connector 14 of the communication cable 12 which is connected to the CCU 5 (see FIG. 19).

A current from the communication cable wire 43 shown in FIG. 4 is then supplied to the electromagnetic coil 47 inside the camera 2. The current flow into the electromagnetic coil 47 generates a magnetic force, the magnetic force then causes an induced current to be generated in the other electromagnetic coil 48, and the induced current is inputted to the control section 44.

Upon receiving the induced current generated in the electromagnetic coil 48, the control section 44 changes the internal changeover switch to switch the power supply from the battery 46 to the power supply from the communication cable wire 43.

Thus, as shown in FIG. 20, the camera 2 is kept firmly and stably indwelling in the abdominal cavity 101 in the patient 100 and the endoscope system 1 of the present embodiment carries out laparoscopic surgery. For example, one end of an aeroperitoneum tube (not shown) is attached to the trocar 110 and a carbon dioxide gas or the like is injected into the abdominal cavity 101 as an aeroperitoneum gas for the purpose of securing the field of view of the camera 2 and for the purpose of securing the area for operating an operation instrument or the like introduced into the abdominal cavity 101. With the camera 2 lifted up to the abdominal wall 102 and left indwelling in the abdominal cavity 101, the operator then inserts the treatment instrument 120 into the trocar 110 and performs laparoscopic surgery.

When the laparoscopic surgery is finished, the operator pulls the outside apparatus 3 out of the wire 67 of the drip-proof cap 60 while pushing the fixing lever 26 of the outside apparatus 3 into the casing 21. The operator then grasps the camera 2 in the abdominal cavity 101 using the treatment instrument 120 such as grasping forceps and pulls the camera 2 out of the abdominal cavity 101 to the outside of the body via the trocar 110.

According to the above-described endoscope system 1 of the present embodiment, it is possible to observe the interior of the body cavity, here, interior tissue in the abdominal cavity 101 using the camera 2 at a wide angle and easily grasp, for example, the whole dissection line during operation of a large organ or during dissection of the large intestine. Furthermore, when the camera 2 introduced into the abdominal cavity 101 is set up, the endoscope system 1 allows the operator to conduct low-invasive surgical operation without increasing burden on the patient.

As a result, using the endoscope system 1 of the present invention makes treatment by laparoscopic surgery easier. Furthermore, the endoscope system 1 eliminates the necessity of puncturing a plurality of trocars through the abdominal wall 102 and allows the operator to conduct low-invasive laparoscopic surgery without imposing burden on the patient 100.

Furthermore, in the endoscope system 1, when the camera 2 is introduced into the abdominal cavity 101, since the electric terminal section 61 of the communication cable wire 43 that transmits various signals of the camera 2 via cable is covered with the drip-proof cap 60, the electric contacts 63 of the electric terminal section 61 need no longer be exposed to the abdominal cavity 101. Thus, it is possible to prevent the electric contacts 63 from being exposed to the abdominal cavity 101 in highly humid conditions, also prevent blood, body fluid or the like from sticking to the electric contacts 63 in the abdominal cavity 101 and thus suppress deterioration, corrosion or the like.

To improve operability in the abdominal cavity 101 which is a limited space when the camera 2 is introduced into the abdominal cavity 101 and the communication cable wire 43 is pulled out of the abdominal cavity 101, the drip-proof cap 60 is provided with the loop-shaped wire 67 to facilitate hooking by the hook section 34 disposed at the distal end of the puncturing rod 33 of the hook needle 4. Furthermore, the drip-proof cap 60 is also provided with the edge 66 to dissect the abdominal wall 102 to facilitate penetration.

By fitting the drip-proof cap 60 to the electric terminal section 61 of the communication cable wire 43, the user who is the operator can easily pull the communication cable wire 43 of the camera 2 out of the abdominal cavity 101, which improves operability of the operation.

Furthermore, the camera 2 of the endoscope system 1 can communicate with the CCU 5 outside the body using the communication cable wire 43 during operation except when introduced into the abdominal cavity 101, and can thereby use the image pickup unit 50 capable of photographing the interior of the abdominal cavity 101 with observed images of high image quality.

As described above, the endoscope system 1 of the present embodiment allows the operator to conduct low-invasive surgical operation without increasing burden on the patient and also allows the camera 2 introduced into the body to transmit clear observed images of high image quality through wired communication and can also improve operability of the operation by the user.

Second Embodiment

Figure 21:
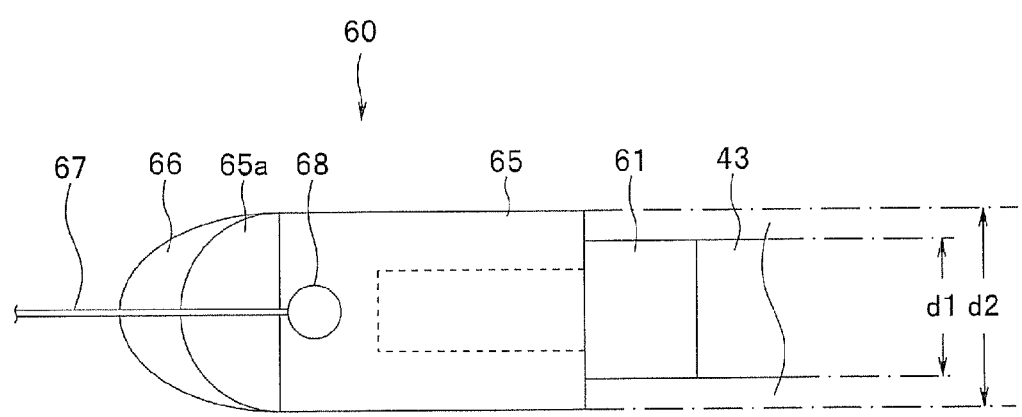
FIG. 21 is related to a second embodiment of the present invention and is a side view illustrating a configuration of a drip-proof cap.

Next, a second embodiment of the endoscope system according to the present invention will be described below using FIG. 21. FIG. 21 is related to the second embodiment of the present invention and is a side view illustrating a configuration of a drip-proof cap. In the following description, the same components as those of the endoscope system 1 of the aforementioned first embodiment will be assigned the same reference numerals and detailed descriptions thereof will be omitted.

As shown in FIG. 21, the drip-proof cap 60 of the present embodiment has a diameter (outside diameter) d2 greater than a diameter (outside diameter) d1 of the communication cable wire 43 (d1<d2).

That is, when the drip-proof cap 60 is fitted to the electric terminal section 61, the outside diameter of the cover body 65 is greater than the outside diameter of the communication cable wire 43 and the communication cable wire 43 can more easily pass through the puncturing hole 103 of the abdominal wall 102 (see FIG. 13 to FIG. 15).

That is, the puncturing hole 103 of the abdominal wall 102 becomes a hole greater than the diameter d1 of the communication cable wire 43 by the edge 66 of the drip-proof cap 60 that dissects the tissue and is further expanded when the cover body 65 of diameter d2 passes therethrough. Thus, the communication cable wire 43 can more easily pass through the puncturing hole 103 expanded through the passage of the cover body 65.

Thus, by making the diameter d2 of the drip-proof cap 60 greater than the diameter d1 of the communication cable wire 43, when the operator pulls the communication cable wire 43 out of the abdominal cavity 101, the communication cable wire 43 can more easily pass through the puncturing hole 103 of the abdominal wall 102.

Third Embodiment

Figure 22:
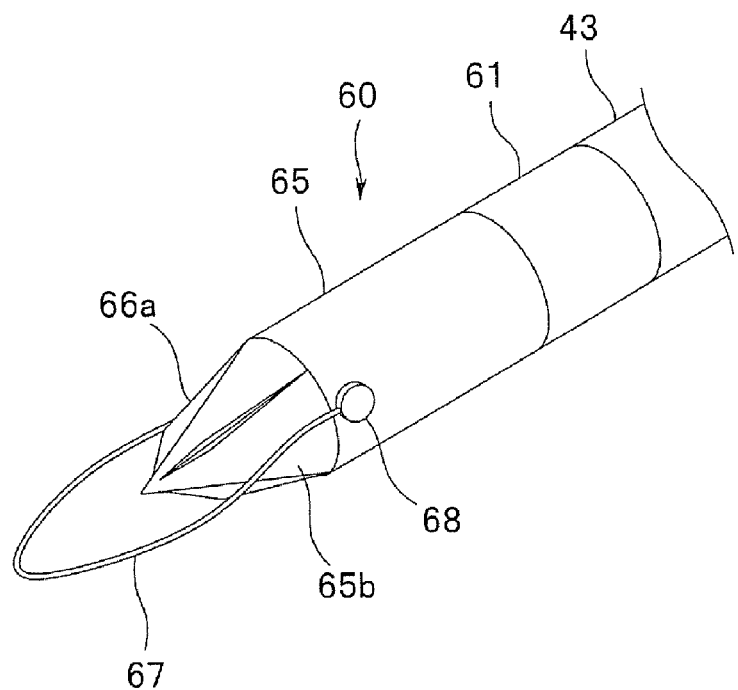
FIG. 22 is related to a third embodiment of the present invention and is a perspective view illustrating a configuration of an end of an electric cable wire fitted with a drip-proof cap for covering an electric terminal section.
Figure 23:
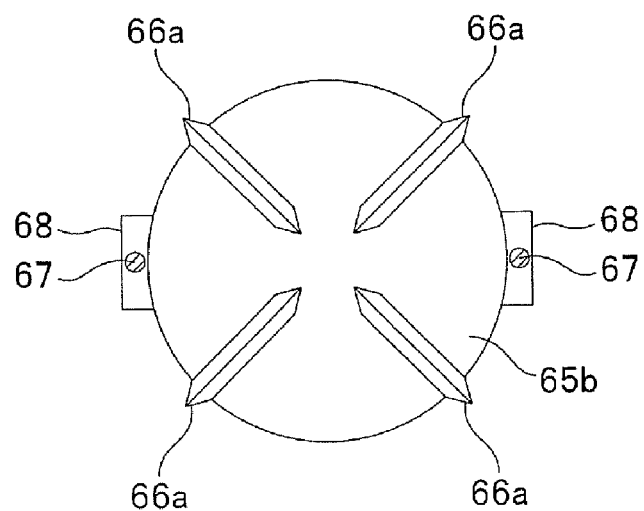
FIG. 23 is a front view illustrating the configuration of the drip-proof cap according to the third embodiment of the present invention.

Next, a third embodiment of the endoscope system according to the present invention will be described below using FIG. 22 and FIG. 23. FIG. 22 and FIG. 23 are related to the third embodiment of the present invention, FIG. 22 is a perspective view illustrating a configuration of an end of an electric cable wire fitted with a drip-proof cap for covering an electric terminal section and FIG. 23 is a front view illustrating the configuration of the drip-proof cap. In the following descriptions, the same components as those of the endoscope system 1 of the aforementioned first embodiment will be assigned the same reference numerals and detailed descriptions thereof will be omitted.

As shown in FIG. 22, the drip-proof cap 60 of the present embodiment has a conical distal end face 65b whose distal end portion is cone-shaped provided with four edges 66a evenly spaced such as around the outer perimeter of the distal end face 65b. The number of the edges 66a is not limited to four, but can be any plural number.

When the drip-proof cap 60 of the present embodiment configured in this way passes through the puncturing hole 103 of the abdominal wall 102, since the distal end face 65b has a conical shape, the drip-proof cap 60 can more easily be introduced into the puncturing hole 103. Since the plurality of (here, four) edges 66a dissect the tissue of the puncturing hole 103 of the abdominal wall 102 and expand the abdominal wall 102, this configuration allows the drip-proof cap 60 to more easily pass through the puncturing hole 103 and improve penetrability of the abdominal wall 102.

Fourth Embodiment

Figure 24:
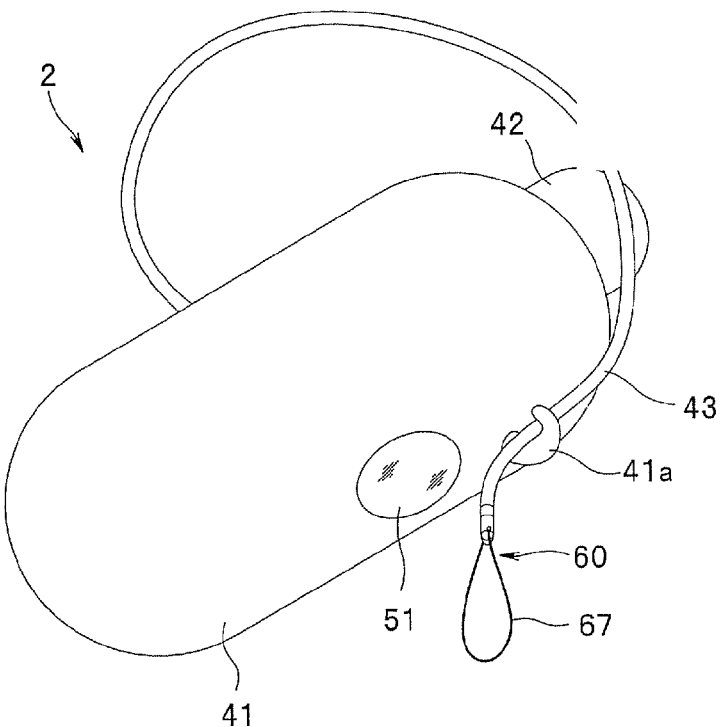
FIG. 24 is related to a fourth embodiment of the present invention and is a perspective view illustrating a configuration of a camera set up in the abdominal cavity.
Figure 25:
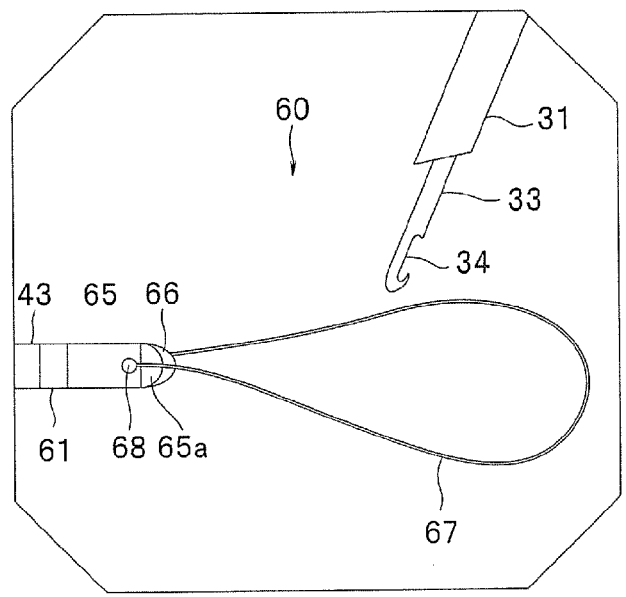
FIG. 25 is a diagram illustrating an image photographed by the camera set up in the abdominal cavity according to the fourth embodiment of the present invention.
Figure 26:
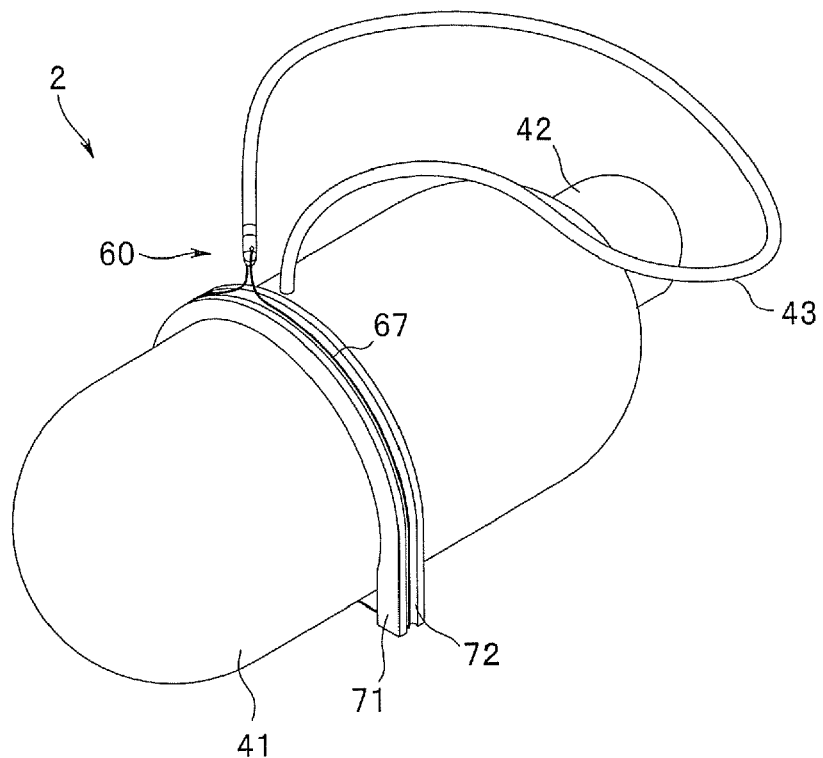
FIG. 26 is a perspective view illustrating a configuration of a camera set up in the abdominal cavity of a modification example of the fourth embodiment of the present invention.
Figure 27:
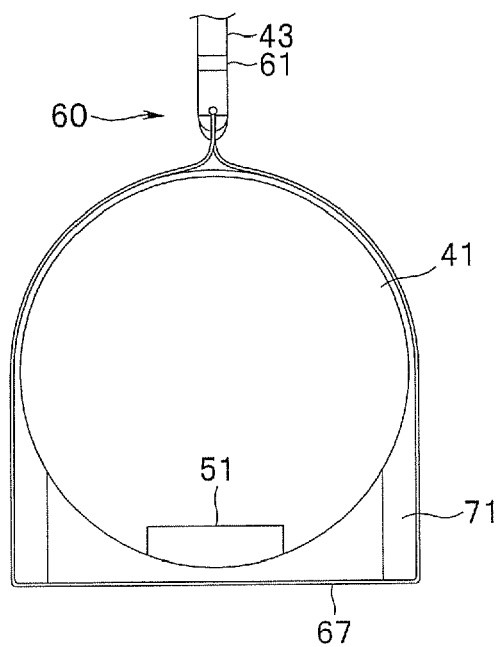
FIG. 27 is a front view illustrating a configuration of the camera set up in the abdominal cavity in FIG. 26 according to the modification example of the fourth embodiment of the present invention.
Figure 28:
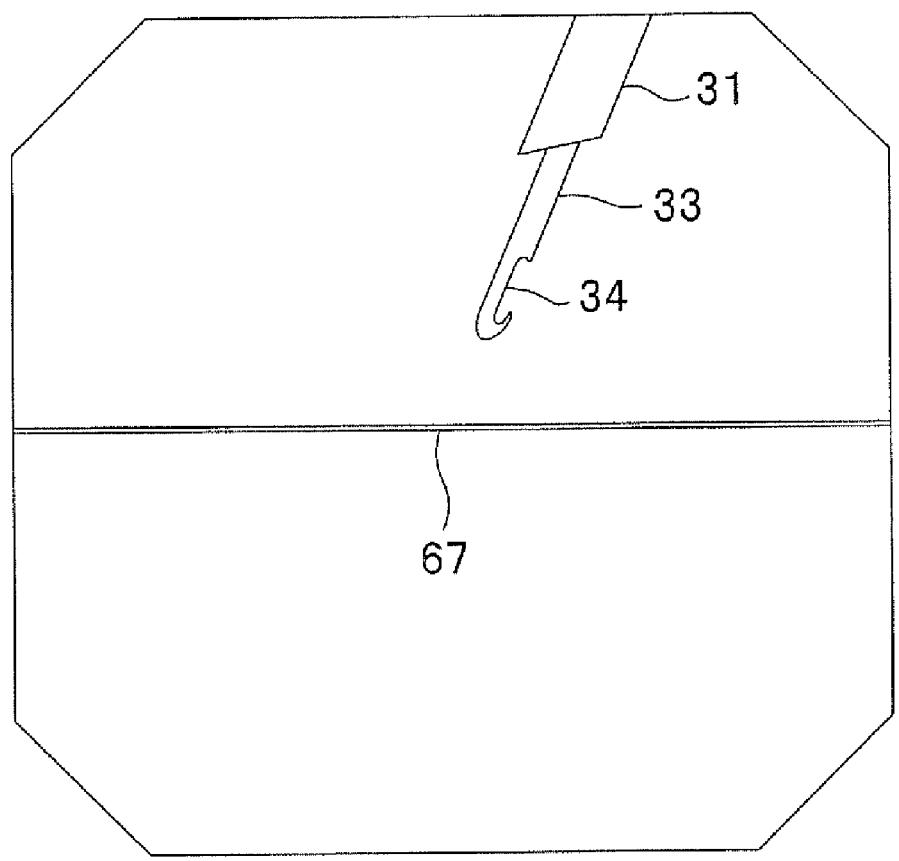
FIG. 28 is a diagram illustrating an image photographed by the camera set up in the abdominal cavity in FIG. 26 according to the modification example of the fourth embodiment of the present invention.

Next, a fourth embodiment of the endoscope system according to the present invention will be described below using FIG. 24 to FIG. 28. FIG. 24 to FIG. 28 are related to the fourth embodiment of the present invention, FIG. 24 is a perspective view illustrating a configuration of a camera set up in the abdominal cavity, FIG. 25 is a diagram illustrating a photographing image taken by the camera set up in the abdominal cavity, FIG. 26 is a perspective view illustrating a configuration of a camera set up in the abdominal cavity of a modification example, FIG. 27 is a front view illustrating a configuration of the camera set up in the abdominal cavity in FIG. 26 and FIG. 28 is a diagram illustrating a photographing image taken by the camera set up in the abdominal cavity in FIG. 26. In the following descriptions, the same components as those of the endoscope system 1 of the aforementioned first embodiment will be assigned the same reference numerals and detailed descriptions thereof will be omitted.

As shown in FIG. 24, the camera 2 of the present embodiment is provided with a cable hook 41a that makes up a cable holding portion for holding the communication cable wire 43 on the outer enclosure section 41. The cable hook 41a is disposed in the vicinity of the cover member 51 which is an observation window outside the photographing field of view of the camera 2. The cable hook 41a is the hook onto which the communication cable wire 43 is hooked and can hold the communication cable wire 43 with a certain degree of holding force.

Before introducing the camera 2 provided with the cable hook 41a into the abdominal cavity 101, the vicinity of the end of the communication cable wire 43 to which the drip-proof cap 60 is fitted is hooked by the operator onto the cable hook 41a to hold the communication cable wire 43. In this case, the operator hooks and holds the communication cable wire 43 onto the cable hook 41a at a position at which the wire 67 of the drip-proof cap 60 is located at a predetermined distance from the surface of the cover member 51.

Thus, the camera 2 provided with the cable hook 41a can always take images of the wire 67 of the drip-proof cap 60 within the field of view of observation. Therefore, as shown in FIG. 25, since the wire 67 of the drip-proof cap 60 is always displayed in the observed image of the camera 2 on the monitor 6, the operator can easily hook the wire 67 onto the hook section 34 of the hook needle 4 without looking for the position of the wire 67. After the wire 67 is hooked onto the hook section 34 of the hook needle 4, the holding of the communication cable wire 43 by the cable hook 41a can be easily released by pulling the hook needle 4 or the like.

As shown in FIG. 26 and FIG. 27, the outer enclosure section 41 of the camera 2 may be provided with a U-shaped wire fixing section 71 onto which the wire 67 of the drip-proof cap 60 is hooked and held. The wire fixing section 71 is attached along the circumference of the outer enclosure section 41 of the camera 2 so that two ends thereof are positioned on the side of the cover member 51 which is the observation window. Furthermore, a concave portion 72 is formed on the outer surface of the wire fixing section 71 to facilitate the holding of the wire 67 to be hooked along the U-shape.

As shown in FIG. 27, the wire 67 held to the wire fixing section 71 starts to have a rectilinear shape from both ends of the wire fixing section 71 and disposed ahead of the cover member 51. Even in such a configuration, the camera 2 can always take images of the wire 67 of the drip-proof cap 60 held to the wire fixing section 71 within the field of view of observation.

Thus, as shown in FIG. 28, the wire 67 of the drip-proof cap 60 is always displayed on the screen of the monitor 6 and the operator can easily hook the wire 67 onto the hook section 34 of the hook needle 4 without looking for the position of the wire 67. Furthermore, after the wire 67 is hooked onto the hook section 34 of the hook needle 4, the operator can easily unhook the wire 67 held to the wire fixing section 71 by pulling the hook needle 4 or the like.

Fifth Embodiment

Figure 29:
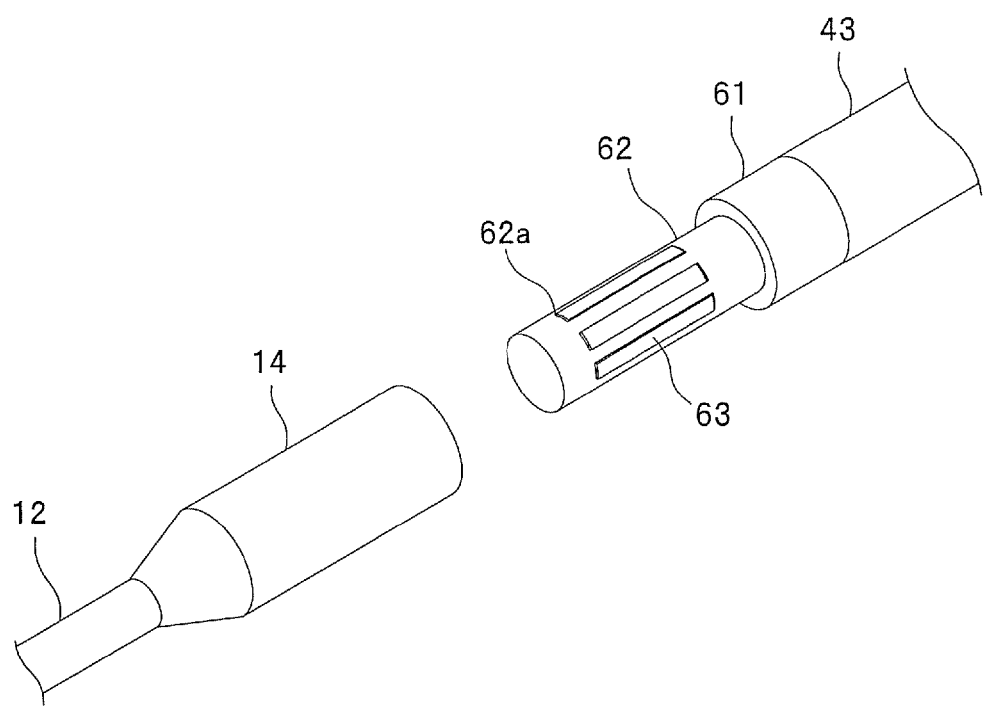
FIG. 29 is related to a fifth embodiment of the present invention and is a perspective view illustrating an electric terminal section and a connector of a communication cable.
Figure 30:
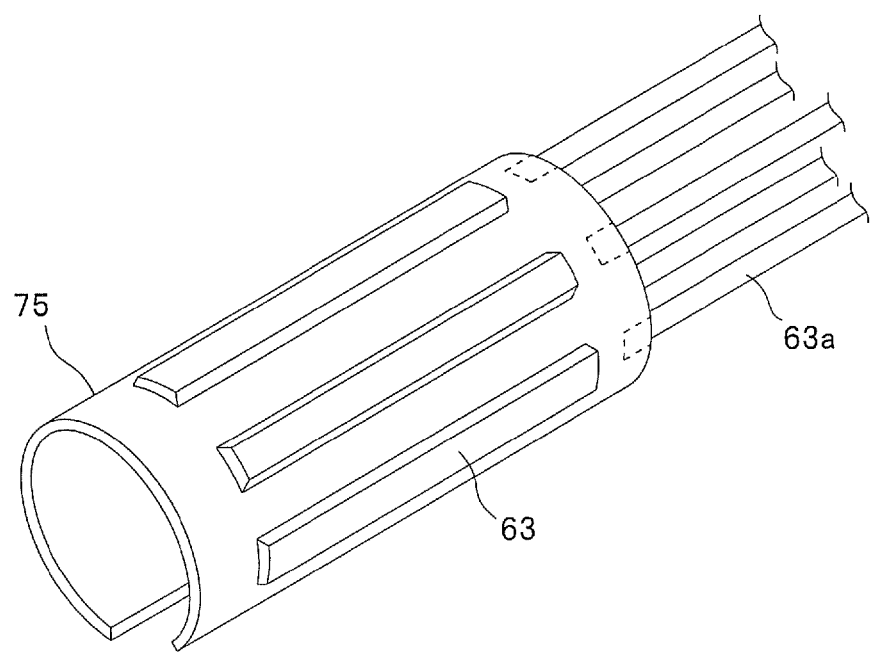
FIG. 30 is a perspective view illustrating a configuration of an arc-shaped flexible substrate provided in the electric terminal section in which an electric contact is formed according to the fifth embodiment of the present invention.
Figure 31:
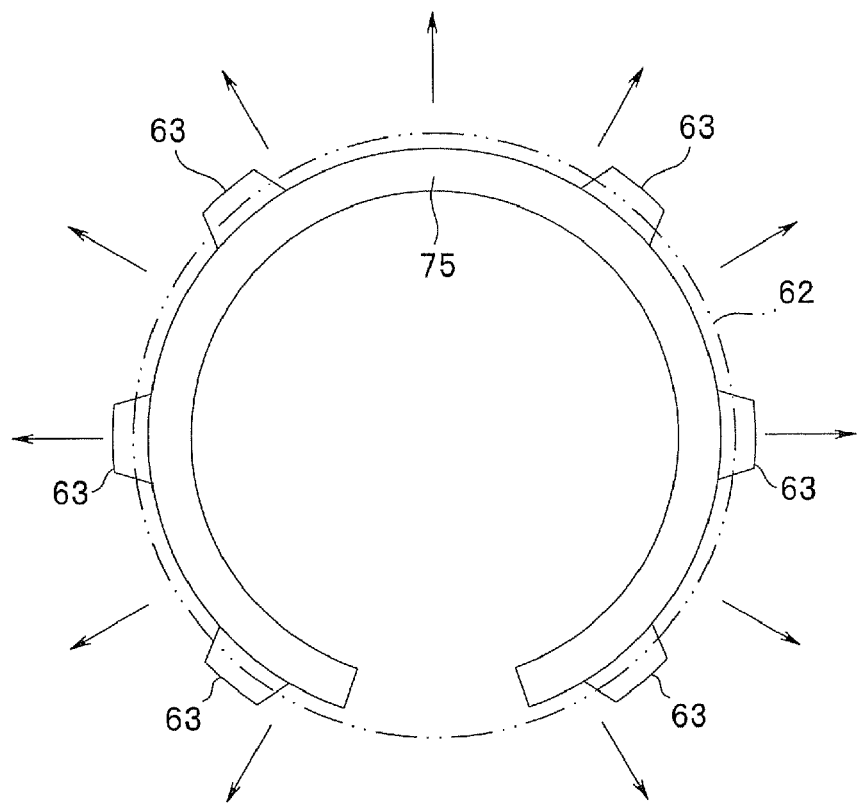
FIG. 31 is a diagram illustrating the operation of the flexible substrate in a single sheet configuration according to the fifth embodiment of the present invention.
Figure 32:
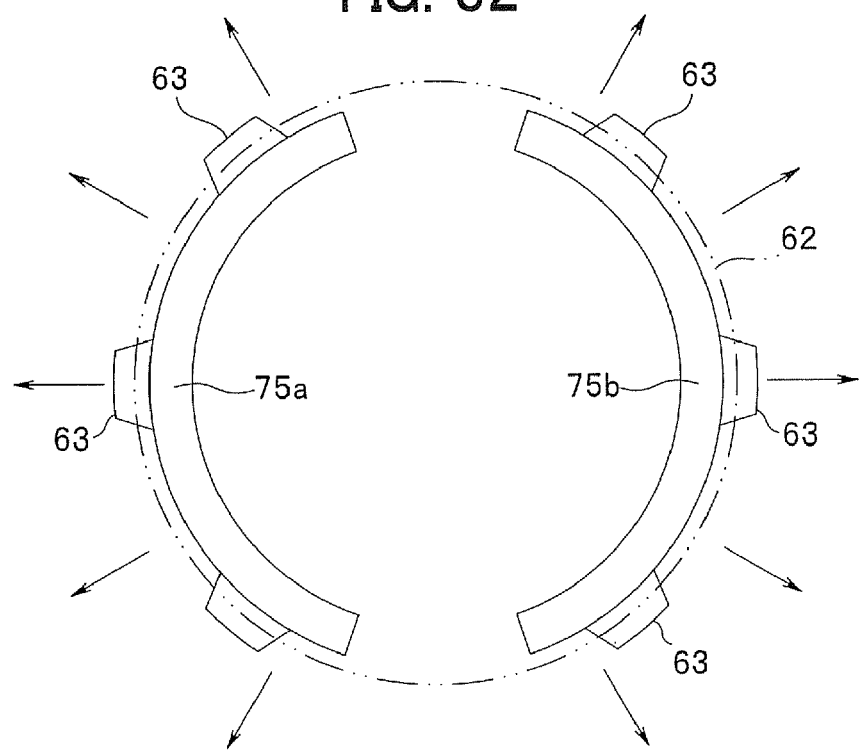
FIG. 32 is a diagram illustrating the operation of the flexible substrate in a double sheet configuration according to the fifth embodiment of the present invention.
Figure 33:
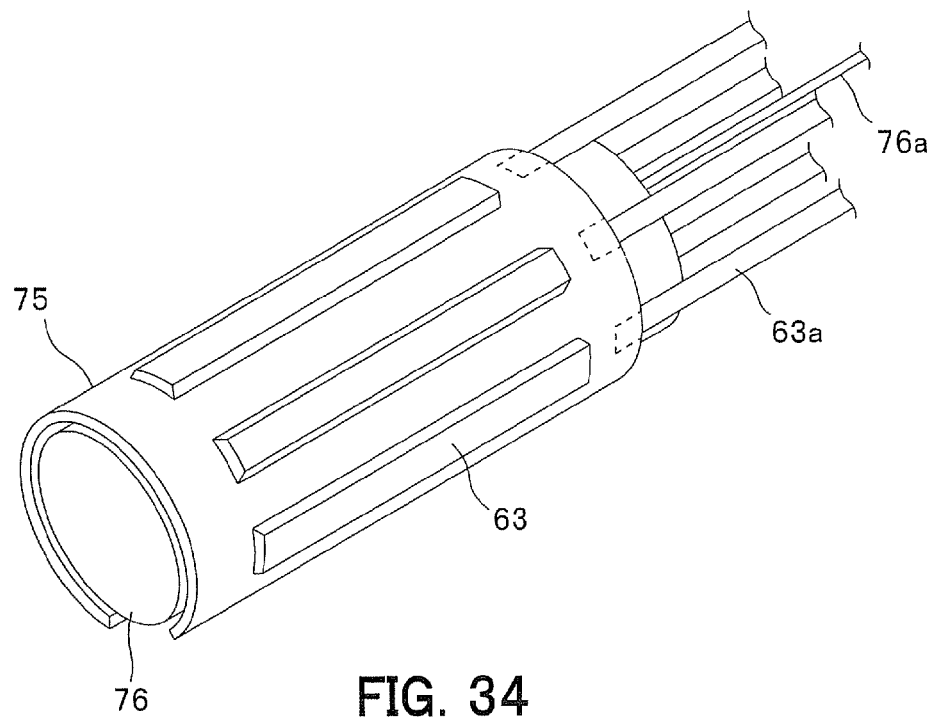
FIG. 33 is a perspective view illustrating a configuration provided with a thermal expansion member inside the flexible substrate according to the fifth embodiment of the present invention.
Figure 34:
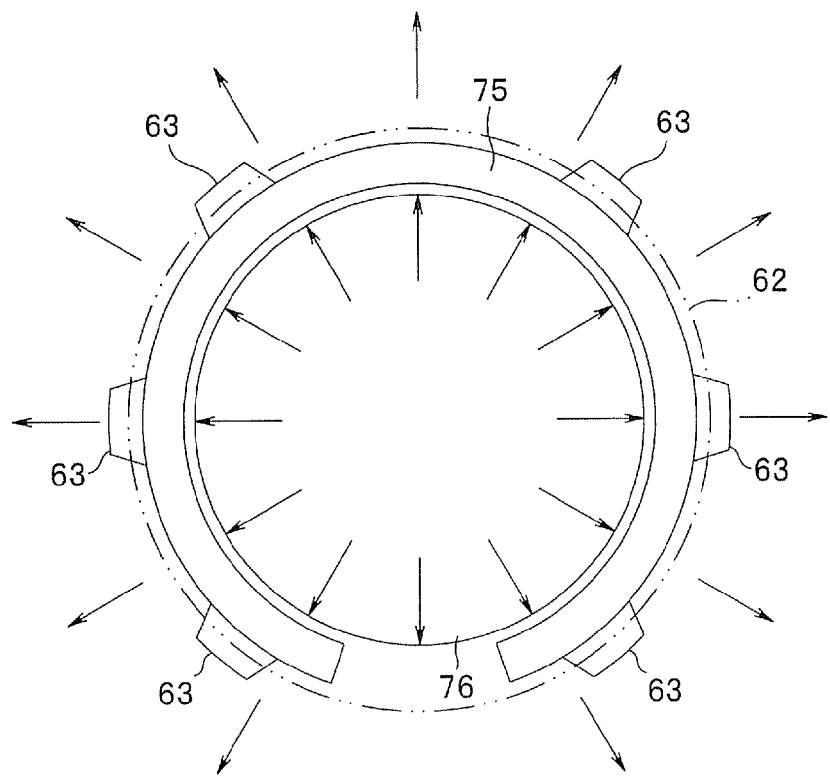
FIG. 34 is a diagram illustrating the operation of the flexible substrate and the thermal expansion member according to the fifth embodiment of the present invention.

Next, a fifth embodiment of the endoscope system according to the present invention will be described below using FIG. 29 to FIG. 34. FIG. 29 to FIG. 34 are related to the fifth embodiment of the present invention, FIG. 29 is a perspective view illustrating an electric terminal section and a connector of a communication cable, FIG. 30 is a perspective view illustrating a configuration of an arc-shaped flexible substrate provided in the electric terminal section in which an electric contact is formed, FIG. 31 is a diagram illustrating the operation of the flexible substrate in a single-sheet configuration, FIG. 32 is a diagram illustrating the operation of the flexible substrate in a double-sheet configuration, FIG. 33 is a perspective view illustrating a configuration provided with a thermal expansion member inside the flexible substrate and FIG. 34 is a diagram illustrating the operation of the flexible substrate and the thermal expansion member. In the following description, the same components as those of the endoscope system 1 of the aforementioned first embodiment will be assigned the same reference numerals and detailed descriptions thereof will be omitted.

In the electric terminal section 61 shown in FIG. 29, an arc-shaped flexible substrate 75 with a plurality of electric contacts 63 provided around the outer perimeter thereof shown in FIG. 30 is disposed inside the male terminal 62.

The male terminal 62 is a hollow terminal herein and a plurality of hole sections 62*a* are formed therein in correspondence with the positions of the plurality of electric contacts 63 to allow the plurality of electric contacts 63 on the flexible substrate 75 disposed inside to protrude therefrom.

A plurality of signal lines 63*a* to be electrically connected to the plurality of electric contacts 63 respectively extend from the flexible substrate 75. Furthermore, the flexible substrate 75 is provided inside the male terminal 62 biased so as to always expand in the circumferential direction as shown in FIG. 31. That is, the plurality of electric contacts 63 provided on the flexible substrate 75 protrude from the plurality of holes 62*a* of the male terminal 62 through biasing in the circumferential direction of the flexible substrate 75.

Furthermore, the flexible substrate 75 is not limited to a one-sheet configuration as shown in FIG. 31, but can also be an arc-shaped two-sheet configuration as shown in FIG. 32.

Furthermore, as shown in FIG. 33 and FIG. 34, a columnar thermal expansion member 76 may also be provided inside the flexible substrate 75. The thermal expansion member 76 is connected to a heat transfer wire 76*a* such as a heat pipe cable and when heat is transferred from the heat transfer wire 76*a*, temperature rises and the thermal expansion member 76 expands. The heat transfer wire 76*a* transfers heat generated in various electric apparatuses such as the image pickup unit 50 and control section 44 in the camera 2 to the thermal expansion member 76.

Thus, providing the thermal expansion member 76 inside the flexible substrate 75 ensures that the flexible substrate 75 is biased in the circumferential direction and ensures that the plurality of electric contacts 63 protrude from the plurality of holes 62*a* of the male terminal 62. It goes without saying that the flexible substrate 75 may have a two-sheet configuration as shown in FIG. 32 and the thermal expansion member 76 may be provided inside these flexible substrates 75.

As described above, by adopting the configuration in which a plurality of electric contacts 63 protrude from the outer circumferential face of the male terminal 62 of the electric terminal section 61 and the plurality of electric contacts 63 are always biased outward, when the male terminal 62 is connected to the connector 14 of the communication cable 12, the plurality of electric contacts 63 reliably contact the electric contacts (not shown) in the connector 14. This prevents defects of electric contact between the male terminal 62 and the connector 14.

Sixth Embodiment

Figure 35:
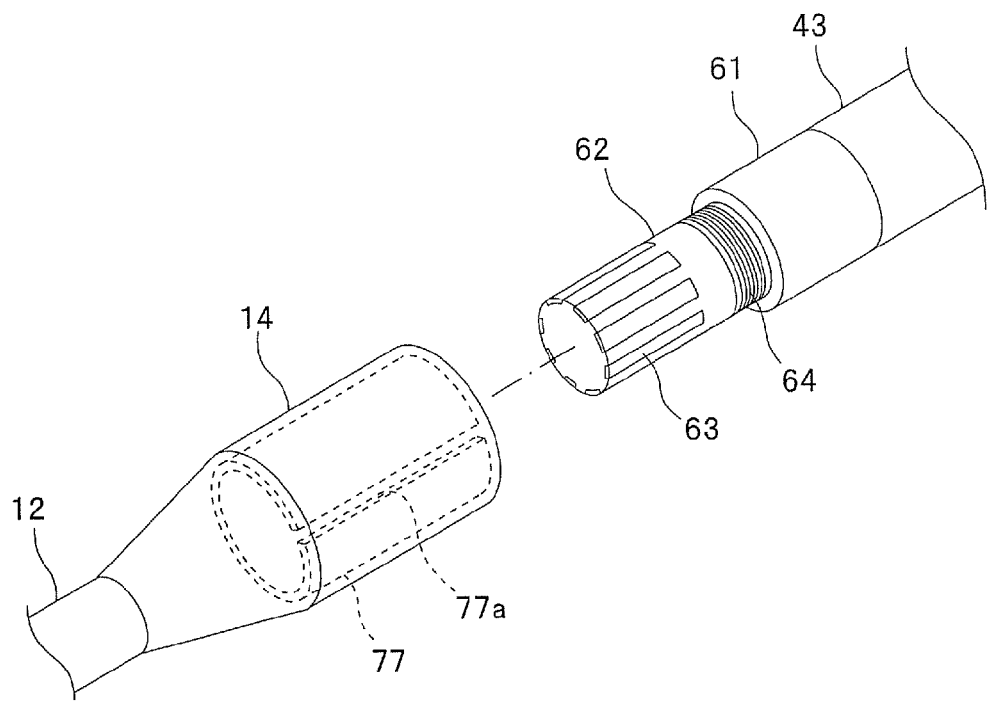
FIG. 35 is related to a sixth embodiment of the present invention and is a perspective view illustrating an electric terminal section and a connector of a communication cable.
Figure 36:
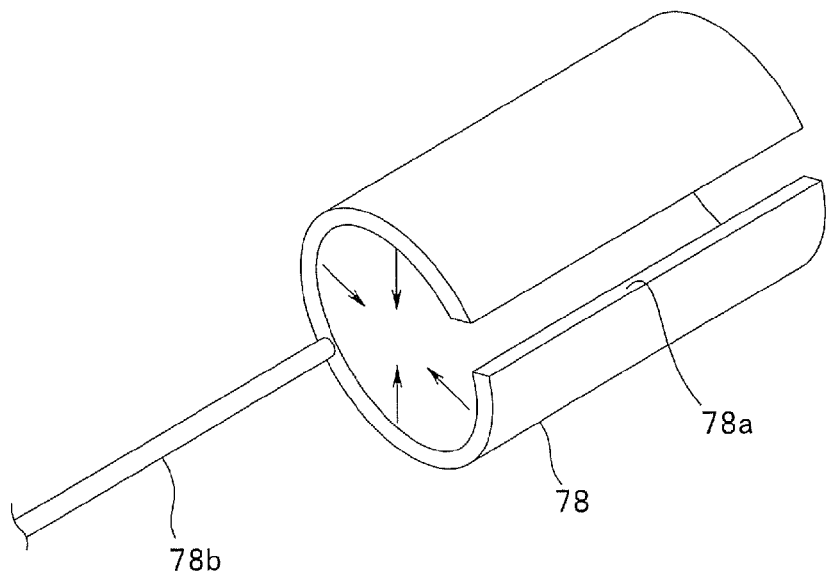
FIG. 36 is a perspective view illustrating a configuration of a thermal expansion member provided inside the connector of the communication cable according to the sixth embodiment of the present invention.

Next, a sixth embodiment of the endoscope system according to the present invention will be described below using FIG. 35 and FIG. 36. FIG. 35 and FIG. 36 are related to the sixth embodiment of the present invention, FIG. 35 is a perspective view illustrating an electric terminal section and a connector of a communication cable and FIG. 36 is a perspective view illustrating a configuration of a thermal expansion member provided inside the connector of the communication cable. In the following description, the same components as those of the endoscope system 1 of the aforementioned first embodiment will be assigned the same reference numerals and detailed descriptions thereof will be omitted.

As shown in FIG. 36, a cylindrical member 77 with a slit 77*a* formed in a longitudinal direction is provided in the connector 14 of the communication cable 12. The inner diameter of the cylindrical member 77 is set so as to generate an urging force that fastens the outer circumferential portion of the male terminal 62 of the electric terminal section 61 to be connected to the connector 14.

That is, when the male terminal 62 is fitted to the connector 14, the inner diameter of the cylindrical member 77 is expanded because the slit 77*a* is formed therein, and an urging force that causes the cylindrical member 77 to contract inward toward the male terminal 62 is generated. Thus, the male terminal 62 is fastened in the connector 14, causing the plurality of electric contacts 63 to reliably contact the electric contacts (not shown) in the connector 14. This prevents defects in electric contact between the male terminal 62 and the connector 14.

As shown in FIG. 36, a cylindrical thermal expansion member 78 with a slit 78*a* formed in a longitudinal direction may also be provided in the connector 14 of the communication cable 12. The outer circumferential portion of the thermal expansion member 78 is disposed so as to contact the inner surface of the connector 14 and the thermal expansion member 78 is connected to the heat transfer wire 78*b*.

The heat transfer wire 78*b* is provided in the communication cable 12 and transfers heat generated in the CCU 5 to which the communication cable 12 is connected to the thermal expansion member 78. The outer circumferential portion of the thermal expansion member 78, the temperature of which has risen with the transmitted heat, is pressed against the inner surface of the connector 14, and therefore the thermal expansion member 78 expands only in the inner diameter direction.

Thus, the thermal expansion member 78 expands inward toward the male terminal 62 when the male terminal 62 is fitted to the connector 14 and fastens the male terminal 62 inside the connector 14. This ensures that the plurality of electric contacts 63 come into contact with the electric contacts (not shown) inside the connector 14 and prevents defects of electric contact between the male terminal 62 and the connector 14.

Seventh Embodiment

Figure 37:
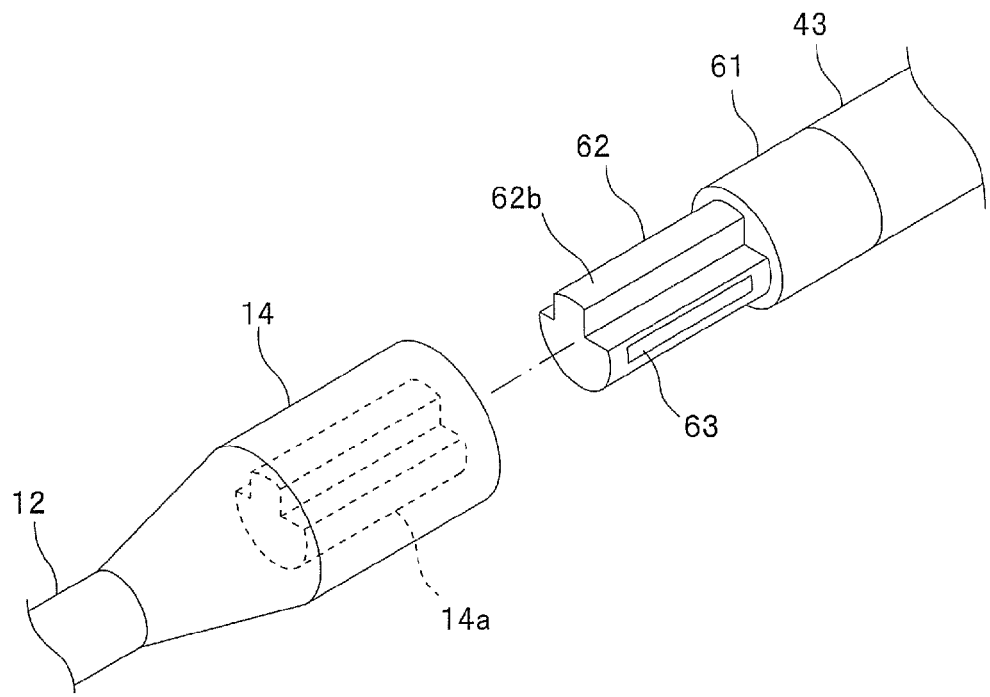
FIG. 37 is related to a seventh embodiment of the present invention and is a perspective view illustrating an electric terminal section and a connector of a communication cable.
Figure 38:
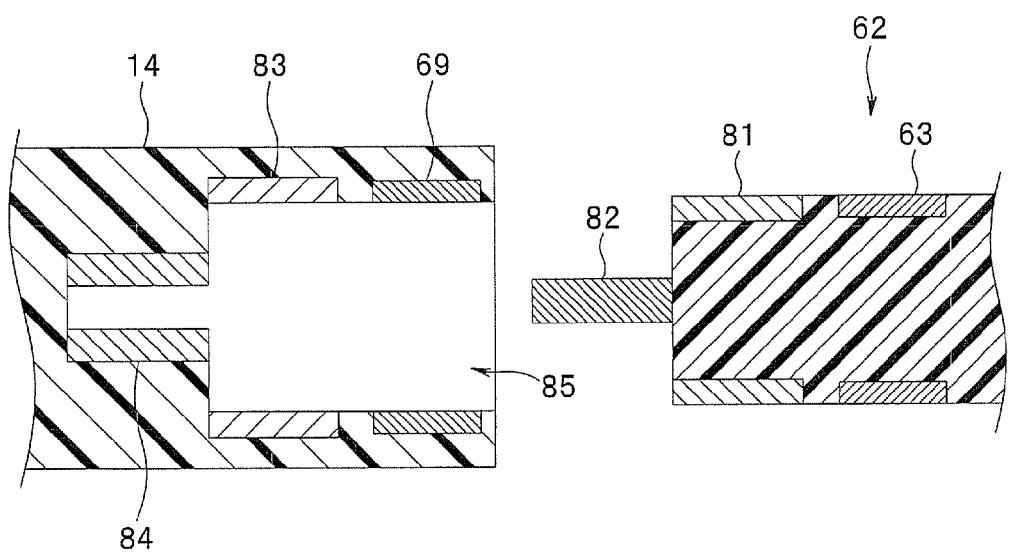
FIG. 38 is a cross-sectional view illustrating an electric terminal section and a connector of a communication cable of a modification example of the seventh embodiment of the present invention.

Next, a seventh embodiment of the endoscope system according to the present invention will be described below using FIG. 37 and FIG. 38. FIG. 37 and FIG. 38 are related to the seventh embodiment of the present invention, FIG. 37 is a perspective view illustrating an electric terminal section and a connector of a communication cable and FIG. 38 is a cross-sectional view illustrating an electric terminal section and a connector of a communication cable of a modification example. Furthermore, in the following description, the same components as those of the endoscope system 1 of the aforementioned first embodiment will be assigned the same reference numerals and detailed descriptions thereof will be omitted.

As shown in FIG. 37, a convex portion 62*b* is formed in a longitudinal direction of the male terminal 62 of the electric terminal section 61. The connector 14 of the communication cable 12 has an engagement section 14*a* in which a hole having the same shape as that of the male terminal 62 is formed.

When the connector 14 is connected to the male terminal 62, such a configuration defines the fitting direction of the male terminal 62 and prevents erroneous connections of the electric contact 63.

Furthermore, as shown in FIG. 38, the male terminal 62 has a toric first magnetic substance 81 on the distal end outer circumferential portion and a bar-shaped second magnetic substance 82 that protrudes from the distal end center and third and fourth magnetic substances 83 and 84 that engage with the magnetic substances 81 and 82 respectively may be provided in the connector 14 of the communication cable 12.

To be more specific, an engagement hole section 85 whose inner shape matches the outer shape of the male terminal 62 is formed in the connector 14. The toric third magnetic substance 83 is provided in the engagement hole section 85 around the area where the first magnetic substance 81 of the male terminal 62 is inserted and the toric fourth magnetic substance 84 is provided around the area where the second magnetic substance 82 of the male terminal 62 is inserted. Furthermore, an electric contact 69 is provided in the engagement hole section 85 at a position where the electric contact 63 of the male terminal 62 is inserted.

Thus, when the male terminal 62 is inserted into the connector 14, the first magnetic substance 81 engages with the third magnetic substance 83 and the second magnetic substance 82 engages with the fourth magnetic substance 84 to thereby prevent the male terminal 62 from detaching from the connector 14. Furthermore, since the second magnetic substance 82 is bar-shaped and inserted into the fourth magnetic substance 84 of the connector 14, it is possible to easily perform axis alignment of the male terminal 62 to be inserted into the connector 14.

The invention described so far in the respective embodiments is not limited to the embodiments and modification examples, but can be modified in various ways without departing from the spirit and scope of the invention in the stage of implementation. Furthermore, the above-described embodiments include inventions in various stages and various inventions can be extracted in an appropriate combination of a plurality of configuration requirements disclosed.

For example, even if some configuration requirements are removed from all configuration requirements disclosed in an embodiment, if the problems to be solved by the invention can be solved and advantages described in the advantages of the invention are obtained, the configuration from which such configuration requirements are removed can be extracted as the invention.

The present invention is provided with the following features.

(Supplementary Note)

An operation method for introducing a medical apparatus into a body, including:

attaching a drip-proof cap to an electric terminal section provided at an end of a communication cable that sends/receives a signal to/from an external device provided in the medical apparatus;

introducing the medical instrument into the body;

puncturing a puncture needle so as to penetrate the body wall into the body into which the medical instrument has been introduced;

locking a hook of the puncture needle at a locking section while photographing the locking section provided at the drip-proof cap using the image pickup unit;

pulling the puncture needle out of the body;

pulling the communication cable out of the body while dissecting the body wall through a dissection section provided at the drip-proof cap;

taking the drip-proof cap out of the electric terminal section; and electrically connecting the electronic terminal section to the external device.

What is claimed is:

1. A medical apparatus introduced into a body, comprising:
   an image pickup unit that picks up an image of an interior of the body;
   a communication cable that sends/receives a signal to/from an external device;
   an electric terminal section disposed at an end section of the communication cable and electrically connected to the external device;
   a drip-proof cap attached so as to cover the electric terminal section and be detachably attached to the electric terminal section;
   a locking section provided at the drip-proof cap that locks a puncture needle for pulling the communication cable introduced into the body out of the body; and
   a dissection section provided at the drip-proof cap that dissects a body wall tissue when the communication cable is pulled out of the body by the puncture needle.

2. The medical apparatus according to claim 1, wherein the locking section is a loop-shaped wire.

3. The medical apparatus according to claim 1, wherein the dissection section is a blade-shaped member provided on a distal end face of the drip-proof cap.

4. The medical apparatus according to claim 3, wherein a distal end of the drip-proof cap is formed in a conical shape.

5. The medical apparatus according to claim 4, wherein a plurality of the blade-shaped members are provided on the conical surface of the drip-proof cap.

6. The medical apparatus according to claim 1, further comprising a holding section that holds the communication cable so that the locking section is positioned within a field of view of the image pickup unit.

7. A medical apparatus introduced into a body, comprising:
   image pickup means for picking up an image of an interior of the body;
   communication means for sending/receiving a signal to/from an external device;
   electric connection means disposed at an end section of the communication means and electrically connected to the external device;
   drip-proof means attached so as to cover the electric connection means and be detachably attached to the electric connection means;
   locking means provided at the drip-proof means for locking puncture means for pulling the communication means introduced into the body out of the body; and
   dissection means provided at the drip-proof means for dissecting a body wall tissue when the communication means is pulled out of the body by the puncture means.

* * * * *